(12) United States Patent
Lee et al.

(10) Patent No.: US 12,431,539 B2
(45) Date of Patent: Sep. 30, 2025

(54) ALL-SOLID SECONDARY BATTERY AND METHOD OF PREPARING THE SAME

(71) Applicant: Samsung Electronics Co., Ltd., Suwon-si (KR)

(72) Inventors: Myungjin Lee, Seoul (KR); Jusik Kim, Hwaseong-si (KR); Sewon Kim, Suwon-si (KR); Victor Roev, Hwaseong-si (KR); Changhoon Jung, Seoul (KR); Intaek Han, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 908 days.

(21) Appl. No.: 17/118,527

(22) Filed: Dec. 10, 2020

(65) Prior Publication Data

US 2022/0006125 A1  Jan. 6, 2022

(30) Foreign Application Priority Data

Jul. 3, 2020  (KR) .......................... 10-2020-0082261

(51) Int. Cl.
*H01M 10/0585*   (2010.01)
*C07D 295/037*   (2006.01)
(Continued)

(52) U.S. Cl.
CPC .... *H01M 10/0585* (2013.01); *C07D 295/037* (2013.01); *H01M 4/133* (2013.01); *H01M 4/134* (2013.01); *H01M 4/364* (2013.01); *H01M 4/366* (2013.01); *H01M 4/382* (2013.01); *H01M 4/405* (2013.01); *H01M 4/587* (2013.01); *H01M 4/62* (2013.01); *H01M 10/0525* (2013.01); *H01M 10/0562* (2013.01); *H01M 10/0564* (2013.01); *H01M 2004/021* (2013.01); *H01M 2004/027* (2013.01); *H01M 2300/0071* (2013.01)

(58) Field of Classification Search
CPC .......................... H01M 4/364; H01M 10/0585
See application file for complete search history.

(56) References Cited

U.S. PATENT DOCUMENTS 9,391,329 B2   7/2016  Yoon et al.
10,347,904 B2  7/2019  Cho et al.
(Continued)

FOREIGN PATENT DOCUMENTS

CN   109004276 A      12/2018
JP   2016139461 A  *  8/2016
(Continued)

*Primary Examiner* — Stephan J Essex
(74) *Attorney, Agent, or Firm* — CANTOR COLBURN LLP

(57) ABSTRACT

An all-solid secondary battery includes a cathode layer including a cathode active material layer; an anode layer; and a solid electrolyte layer disposed between the cathode layer and the anode layer, wherein the anode layer includes an anode current collector and a first anode active material layer is disposed on the anode current collector, wherein the first anode active material layer includes an organic electrolyte and an anode active material that is capable of forming an alloy with lithium or a compound with lithium, and wherein the organic electrolyte includes an organic salt including an organic cation and an anion.

20 Claims, 9 Drawing Sheets
(3 of 9 Drawing Sheet(s) Filed in Color)

(51) Int. Cl.
  *H01M 4/02*     (2006.01)
  *H01M 4/133*    (2010.01)
  *H01M 4/134*    (2010.01)
  *H01M 4/36*     (2006.01)
  *H01M 4/38*     (2006.01)
  *H01M 4/40*     (2006.01)
  *H01M 4/587*    (2010.01)
  *H01M 4/62*     (2006.01)
  *H01M 10/0525*  (2010.01)
  *H01M 10/0562*  (2010.01)
  *H01M 10/0564*  (2010.01)

(56) References Cited

U.S. PATENT DOCUMENTS

| | | |
|---|---|---|
| 10,497,930 B2 | 12/2019 | Lee et al. |
| 10,741,846 B2 | 8/2020 | Lee et al. |
| 2005/0042515 A1 | 2/2005 | Hwang et al. |
| 2015/0050535 A1* | 2/2015 | Amiruddin ........... H01M 4/364 429/188 |
| 2017/0301947 A1* | 10/2017 | Makino ................. H01M 4/622 |
| 2018/0212219 A1* | 7/2018 | Kim ..................... H01M 50/411 |
| 2019/0157723 A1 | 5/2019 | Suzuki et al. |
| 2019/0165418 A1 | 5/2019 | Petricci et al. |
| 2019/0393485 A1 | 12/2019 | He et al. |

FOREIGN PATENT DOCUMENTS

| | | |
|---|---|---|
| KR | 100497251 B1 | 6/2005 |
| KR | 1020050070500 A | 7/2005 |
| KR | 1020130128273 A | 5/2013 |
| KR | 1020160037636 A | 4/2016 |
| KR | 1020170126404 A | 11/2017 |

* cited by examiner

ALL-SOLID SECONDARY BATTERY AND METHOD OF PREPARING THE SAME

CROSS-REFERENCE TO RELATED APPLICATION

This application claims priority to and the benefit of Korean Patent Application No. 10-2020-0082261, filed on Jul. 3, 2020, in the Korean Intellectual Property Office, and all the benefits accruing therefrom under 35 U.S.C. § 119, the content of which is incorporated herein in its entirety by reference.

BACKGROUND

1. Field

The present disclosure relates to an all-solid secondary battery and a method of preparing the all-solid secondary battery.

2. Description of Related Art

Recently, in accordance with industrial demand, the development of batteries having high energy density and improved safety has been pursued. For example, lithium-ion batteries have been put to practical use in the automotive field as well as in information-related equipment and communication equipment. In the field of automobiles, safety is particularly important because an adverse event in an automobile could cause harm to human life.

Lithium-ion batteries that have been commercialized use an electrolyte solution that includes a flammable organic solvent, and thus, when a short-circuit occurs, there is a possibility of an adverse event, such as overheating and possible combustion of the flammable solvents. Accordingly, there remains a need for an improved all-solid secondary battery using a solid electrolyte instead of an electrolyte solution.

SUMMARY

Provided is a lithium battery in which internal resistance problems that may be increased by the contact deficiency between an anode active material layer and a solid electrolyte layer are resolved and has improved lifespan characteristics due to regular deposition of lithium.

Additional aspects will be set forth in part in the description which follows and, in part, will be apparent from the description.

According to an aspect, an all-solid secondary battery includes
  a cathode layer including a cathode active material layer;
  an anode layer; and
  a solid electrolyte layer disposed between the cathode layer and the anode layer,
  wherein the anode layer includes an anode current collector and a first anode active material layer disposed on the anode current collector,
  wherein the first anode active material layer includes an organic electrolyte and an anode active material capable of forming an alloy with lithium or a compound with lithium, and
  wherein the organic electrolyte includes an organic salt including an organic cation and an anion.

According to another aspect, a method of preparing an all-solid secondary battery includes:
  providing a cathode layer comprising a cathode active material layer;
  providing a first anode active material layer including an organic electrolyte and an anode active material that is capable of forming an alloy with lithium or a compound with lithium;
  disposing the first anode active material layer on a solid electrolyte layer to prepare a stack; and
  disposing the cathode layer on the solid electrolyte layer of the stack
  wherein the organic electrolyte includes an organic salt including an organic cation and an anion, and
  wherein an anode layer comprises a current collector and the first anode active material layer.

According to yet another aspect, a method of preparing an all-solid secondary battery includes:
  providing a cathode layer comprising a cathode active material layer;
  providing a first anode active material layer comprising an organic electrolyte and an anode active material that is capable of forming an alloy with lithium or a compound with lithium and a second anode active material layer comprising a metal layer comprising lithium or a lithium alloy;
  disposing the first anode active material layer on the second anode active material layer to prepare a first stack;
  disposing a solid electrolyte layer on the first anode active material layer of the first stack to prepare a second stack; and
  disposing the cathode layer on the solid electrolyte layer of the second stack,
  wherein the organic electrolyte comprises an organic salt comprising an organic cation and an anion, and
  wherein an anode layer comprises a current collector, the first anode active material layer, and the second anode active material layer.

BRIEF DESCRIPTION OF THE DRAWINGS

The patent or application file contains at least one drawing executed in color. Copies of this patent or patent application publication with color drawings will be provided by the U.S. Patent and Trademark Office upon request and payment of the necessary fee.

The above and other aspects, features, and advantages of certain embodiments of the disclosure will be more apparent from the following description taken in conjunction with the accompanying drawings, in which.

DETAILED DESCRIPTION

Figure 1:
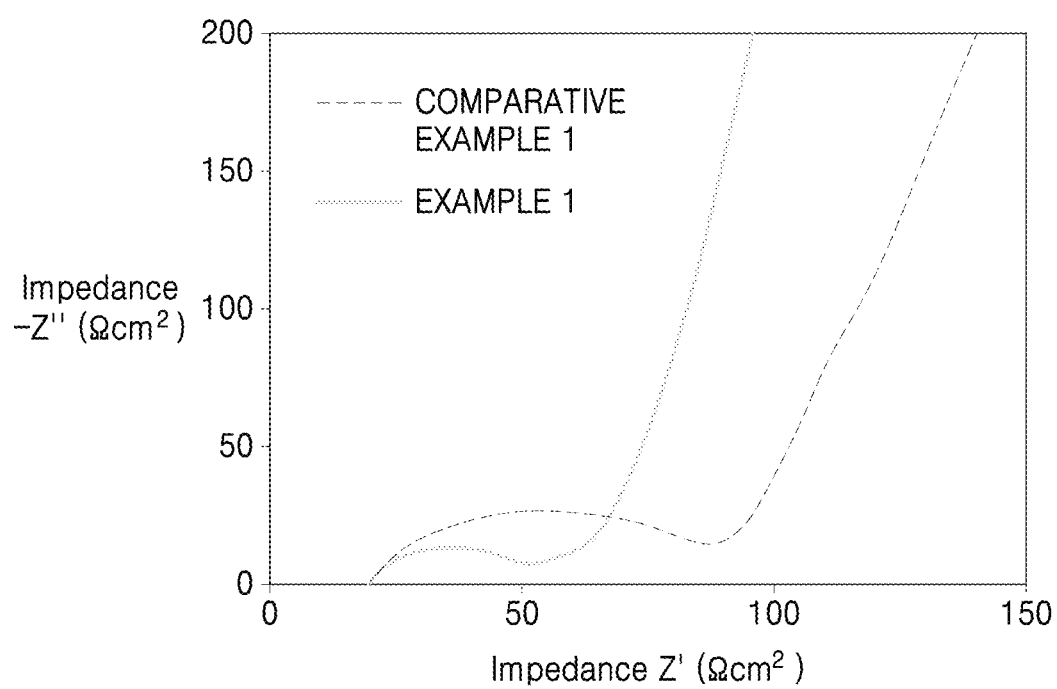
FIG. 1 is a graph of impedance $-Z''$ (ohm square centimeter, a $\Omega \cdot cm^2$) versus impedance $Z'$ ($\Omega \cdot cm^2$) and shows a Nyquist plot of the results of impedance measurements performed on all-solid secondary batteries of Example 1 and Comparative Example 1.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects.

Hereinafter, as the present inventive concept allows for various changes and numerous embodiments, particular embodiments are illustrated in the drawings and described in detail in the written description. However, this is not intended to limit the present inventive concept to particular modes of practice, and it is to be appreciated that all changes, equivalents, and substitutes that do not depart from the spirit and technical scope are encompassed in the present inventive concept.

The terms used herein are merely used to describe particular embodiments and are not intended to limit the present inventive concept. As used herein, "a," "an," "the," and "at least one" do not denote a limitation of quantity and are intended to cover both the singular and plural, unless the context clearly indicates otherwise. For example, "an element" has the same meaning as "at least one element," unless the context clearly indicates otherwise. As used herein, the term "and/or" includes any and all combinations of one or more of the associated listed items. Expressions such as "at least one of," when preceding a list of elements, modify the entire list of elements and do not modify the individual elements of the list.

An expression used in the singular encompasses the expression of the plural unless it has a clearly different meaning in the context. As used herein, it is to be understood that the terms such as "including," "having," and "comprising" are intended to indicate the existence of the stated features, numbers, steps, actions, components, parts, ingredients, materials, or combinations thereof disclosed in the specification, and are not intended to preclude the possibility that one or more other features, numbers, steps, actions, components, parts, ingredients, materials, or combinations thereof may exist or may be added. The symbol "/" used herein may be interpreted as "and" or "or" according to the context.

In the drawings, the thicknesses of layers and regions are exaggerated or reduced for clarity. Like reference numerals in the drawings denote like elements. Throughout the specification, it will be understood that when a component, such as a layer, a film, a region, or a plate, is referred to as being "on" another component, the component may be directly on the other component or intervening components may be present thereon.

Throughout the specification, while such terms as "first," "second," etc., may be used herein to describe various elements, components, regions, layers and/or sections, these elements, components, regions, layers and/or sections should not be limited by these terms. These terms are used only to distinguish one element, component, region, layer or section from another element, component, region, layer, or section. Thus, unless otherwise specified herein, "a first element," "component," "region," "layer" or "section" discussed below could be termed a second element, component, region, layer, or section without departing from the teachings herein. In the present specification and drawings, constituent elements having substantially the same functional configuration will be denoted with the same reference numeral, thereby omitting redundant description.

Furthermore, spatially relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value.

As used herein, the terms "an embodiment", "embodiments", and the like indicate that elements described with regard to an embodiment are included in at least one embodiment described in this specification and may or may not present in other embodiments. In addition, it may be understood that the described elements are combined in any suitable manner in various embodiments. Unless otherwise defined, technical and scientific terms used herein have the same meaning as commonly understood by one or ordinary skill in the art to which this application belongs. All patents, patent applications, and other cited references are incorporated herein by reference in their entirety. However, in the event of any conflict or inconsistency between terms used herein and terms of the cited references, the terms used in this specification take precedence over the terms of the cited references. While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modification, variations, improvements, and substantial equivalents.

"Argyrodite," "argyrodite structure," or "argyrodite-type structure" as used herein means that the compound has a crystal structure that is isostructural with argyrodite, $Ag_8GeS_6$.

A garnet compound is a compound of the formula $X_3Y_2(SiO_4)_3$, wherein X is a divalent cation, such as $Ca^{2+}$, $Mg^{2+}$, $Fe^{2+}$, $Mn^{2+}$, or a combination thereof, and Y is a trivalent cation, such as $Al^{3+}$, $Fe^{3+}$, $Cr^{3+}$, or a combination thereof.

In an all-solid secondary battery, a flammable organic solvent is not used, and thus the possibility of a fire or an explosion may be reduced even when a short-circuit occurs. Therefore, such an all-solid secondary battery may safer than a lithium-ion battery that uses a liquid and/or solvent based electrolyte.

However, since solid batteries of the related art use a solid electrolyte, when the contact between an electrode active material and the solid electrolyte and/or contact within the solid electrolyte is not sufficiently maintained, resistance in the battery increases, and short-circuits occur due to irregular deposition of lithium during the charging/discharging process, thus making it difficult to realize a battery with excellent battery characteristics.

Currently, a battery needs to undergo a high-temperature and pressurization process such as hot isostatic pressing (HIP) in the preparation process of an all-solid battery to increase the contact between an anode active material layer and a solid electrolyte layer. The HIP may not be a continuous process, and a high energy is needed for the high-temperature and pressurization processes.

Hereinafter, according to one or more embodiments, an all-solid secondary battery, and a method of preparing the all-solid secondary battery will be described in detail.

According to an embodiment, an all-solid secondary battery includes a cathode layer including a cathode active material layer; an anode layer; and a solid electrolyte layer disposed between the cathode layer and the anode layer, wherein the anode layer includes an anode current collector; and a first anode active material layer disposed on the anode current collector, wherein the first anode active material layer includes an organic electrolyte; and an anode active material capable of forming an alloy or a compound with lithium, and wherein the organic electrolyte includes an organic salt containing an organic cation and an anion.

When the first anode active material layer includes the organic electrolyte, an interfacial resistance due to irregular contact between the first anode active material layer and the solid electrolyte layer may decrease. As a result, an internal resistance of the secondary battery may decrease. Also, since the first anode active material layer effectively accepts a volume change during charge/discharge of the secondary battery, the cracks of the solid electrolyte layer occurring during charge/discharge of the secondary battery may be effectively prevented, and thus a short-circuit in the secondary battery may be prevented. When the first anode active material layer includes the organic electrolyte, relatively regular deposition and dissolution of lithium at an interface between the first anode active material layer and the solid electrolyte layer may occur during the charge/discharge of the secondary battery. In this regard, when a short-circuit caused by irregular deposition of lithium is prevented, stable charging/discharging of a secondary battery at a relatively high current density may be possible. As a result, lifespan characteristics of the secondary battery may be improved.

For example, since the organic electrolyte in the first anode active material layer is disposed in an empty space between anode active material particles, a mixture density of an anode including an organic electrolyte may be higher than a mixture density of an anode that does not include an organic electrolyte. For example, when the organic electrolyte in the first anode active material layer is disposed in an empty space of an interface between the first anode active material layer and the solid electrolyte layer, a mixture density of a secondary battery including an anode including an organic electrolyte may be higher than a mixture density of a secondary battery including an anode not having an organic electrolyte. As a result, an energy density of the secondary battery including an anode including an organic electrolyte may be improved. For example, an anode in which an organic electrolyte is uniformly filled between anode active material particles may be obtained by a cold isostatic press process at room temperature of 25° C. and a relatively low pressure. Thus, contact between the first anode active material layer and the solid electrolyte layer may be improved without high-temperature and high-pressure processes such as a hot isostatic press process, which is required in preparation of a secondary battery including an anode not including an organic electrolyte.

All-Solid Secondary Battery

Figure 4:
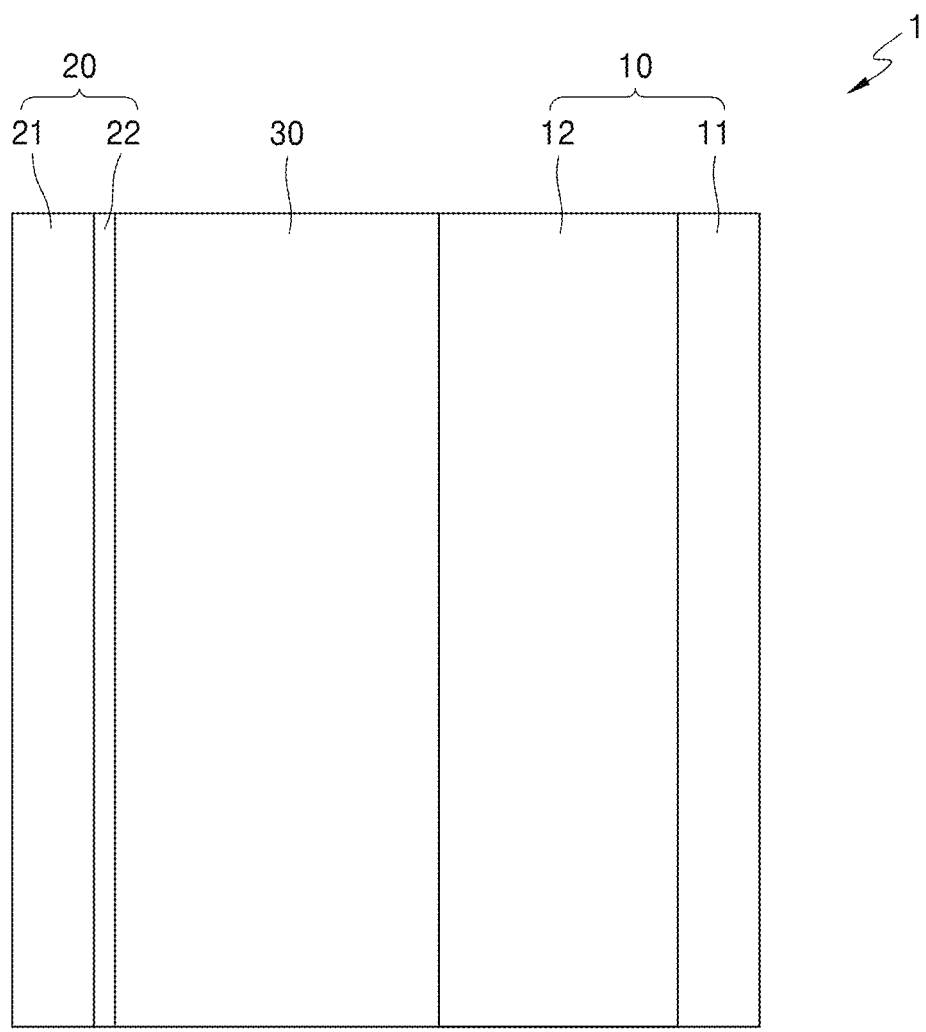
FIG. 4 is a cross-sectional view of an embodiment of an all-solid secondary battery.
Figure 5:
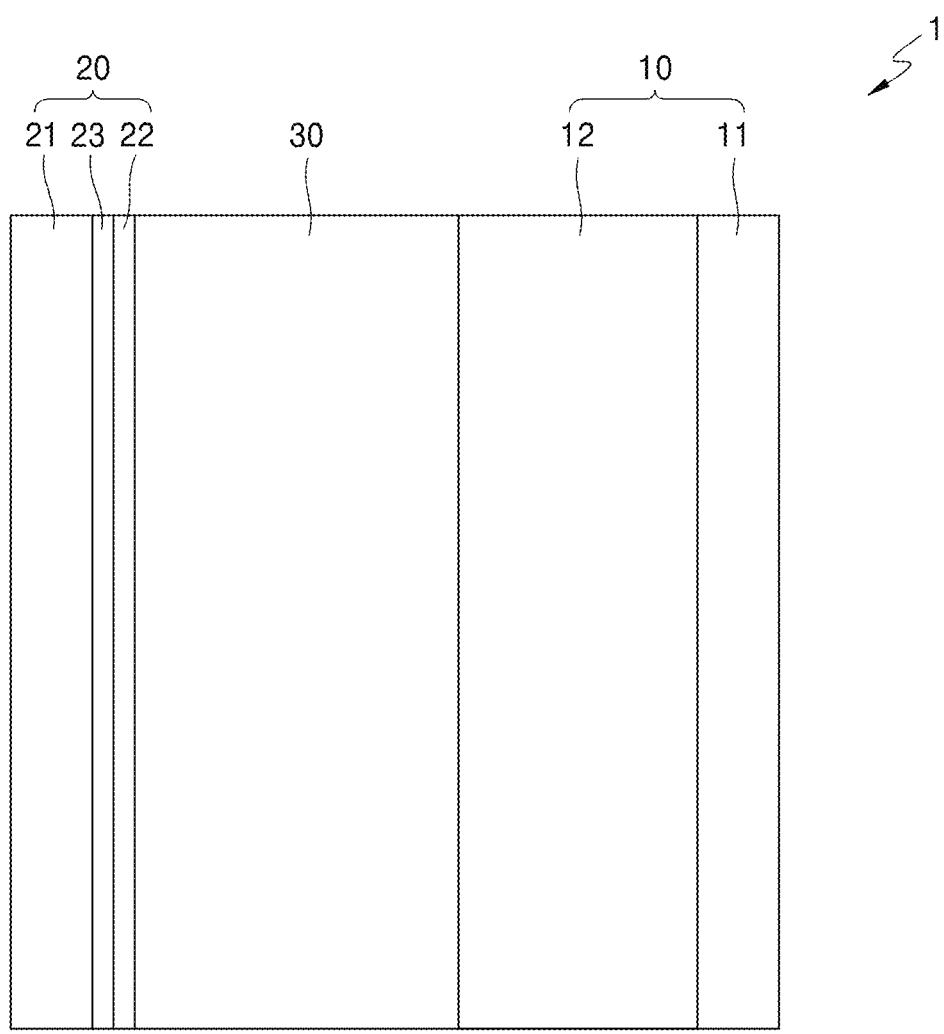
FIG. 5 is a cross-sectional view of an embodiment of an all-solid secondary battery.
Figure 6:
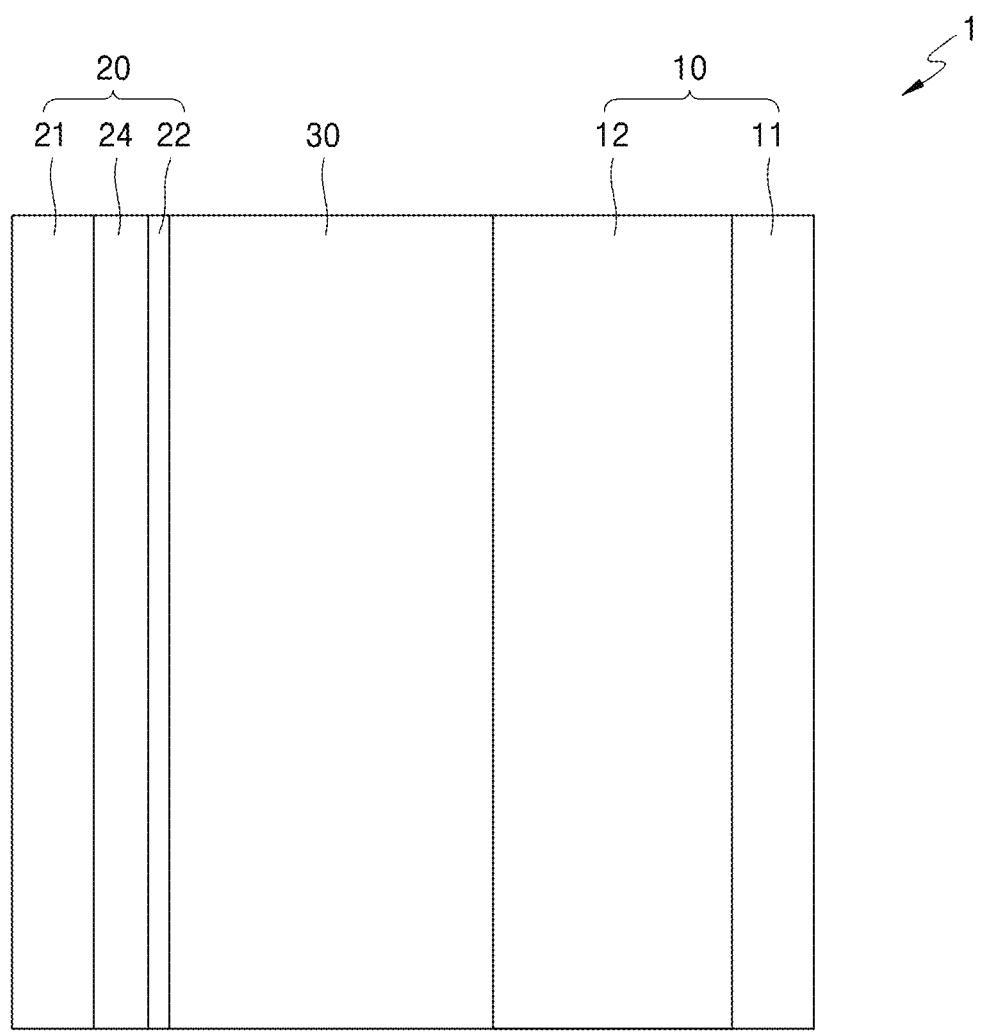
FIG. 6 is a cross-sectional view of an embodiment of an all-solid secondary battery.

Referring to FIGS. 4 to 6, an all-solid secondary battery 1 includes a cathode layer 10 including a cathode active material layer 12; an anode layer 20; and a solid electrolyte layer 30 disposed between the cathode layer 10 and the anode layer 20, wherein the anode layer 20 includes an anode current collector 21; and a first anode active material layer 22 disposed on the anode current collector 21, wherein the first anode active material layer 22 includes an organic electrolyte; and an anode active material capable of forming an alloy with lithium or a compound with lithium, wherein the organic electrolyte includes an organic salt containing an organic cation and an anion.

Anode Layer

Referring to FIGS. 4 to 6, when the first anode active material layer 22 includes an organic salt containing an organic cation and an anion, an interfacial resistance between the first anode active material layer 22 and the solid electrolyte layer 30 decreases, and thus irregular deposition of lithium at the interface is suppressed. Also, due to an increase in a mixture density of the anode layer 20, cycle characteristics of the all-solid secondary battery 1 may be improved, and an energy density may be improved.

The organic cation in the first anode active material layer 22 may include, for example, at least one of an acyclic cation containing a Group 15 element or a heterocyclic ring cation including 1 to 3 heteroatoms. For example, the acyclic cation is a cation that contains a Group 15 element includes a Group 15 element such as N or P and hydrogen or an unsubstituted or halogen-substituted C1-C30 hydrocarbyl group connected to the Group 15 element. The hydrocarbyl group is linear or branched and does not form a ring. The heterocyclic ring cation including 1 to 3 heteroatoms is a cation that forms a C2-C20 heterocyclic ring including heteroatoms such as N, P, O, or S, but not carbon or hydrogen. The heterocyclic ring may be an aliphatic ring or an aromatic ring. The heterocyclic ring may be unsubstituted or substituted with a substituent group or a halogen. The substituent group may be an unsubstituted or halogen-substituted C1-C30 alkyl group, an unsubstituted or halogen-substituted C1-C30 alkoxy group, an unsubstituted or halogen-substituted C6-C30 aryl group, an unsubstituted or halogen-substituted C6-C30 aryloxy group, an unsubstituted or halogen-substituted C3-C30 heteroaryl group, an unsubstituted or halogen-substituted C3-C30 heteroaryloxy group, an unsubstituted or halogen-substituted C4-C30 cycloalkyl group, an unsubstituted or halogen-substituted C3-C30 heterocycloalkyl group, or an unsubstituted or halogen-substituted $C2-C_{100}$ alkylene oxide group, where at least one of a substituent group substituted in the ring, $R_5$, or $R_6^-$, may be a C6-C12 alkyl group partially or completely substituted with a halogen or a C6-C30 aryl group partially or completely substituted with a halogen. The cation may include a cation monomer including one cation or a plurality of repeating units, and one of the repeating units may be a cationic polymer or a cationic oligomer including one cation.

The organic salt in the first anode active material layer 22 may be, for example, a compound represented by at least one of Formula 1 of Formula 2:

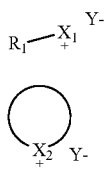

Formula 1

Formula 2

In Formula 1, $X_1$ may be $-N(R_2)(R_3)(R_4)$ or $-P(R_2)(R_3)(R_4)$, and $R_1$, $R_2$, $R_3$, and $R_4$ may be each independently an unsubstituted or halogen-substituted C1-C30 alkyl group, an unsubstituted or halogen-substituted C1-C30 alkoxy group, an unsubstituted or halogen-substituted C6-C30 aryl group, an unsubstituted or halogen-substituted C6-C30 aryloxy group, an unsubstituted or halogen-substituted C3-C30 heteroaryl group, an unsubstituted or halogen-substituted C3-C30 heteroaryloxy group, or an unsubstituted or halogen-substituted C4-C30 cycloalkyl group.

In Formula 2, the structure represented by:

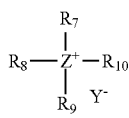

may be a heterocycloalkyl or heteroaryl ring including 1 to 3 heteroatoms and 2 to 30 carbon atoms, the ring may be unsubstituted or substituted with a substituent group, $X_2$ may be $-N(R_5)(R_6)-$, $-N(R_5)=$, $-P(R_5)=$, or $-P(R_5)(R_6)-$, the substituent group substituted in the ring, $R_5$, and $R_6$ may be each independently hydrogen, an unsubstituted or halogen-substituted C1-C30 alkyl group, an unsubstituted or halogen-substituted C1-C30 alkoxy group, an unsubstituted or halogen-substituted C6-C30 aryl group, an unsubstituted or halogen-substituted C6-C30 aryloxy group, an unsubstituted or halogen-substituted C3-C30 heteroaryl group, an unsubstituted or halogen-substituted C3-C30 heteroaryloxy group, an unsubstituted or halogen-substituted C4-C30 cycloalkyl group, or an unsubstituted or halogen-substituted C3-C30 heterocycloalkyl group, and $Y^-$ is an anion.

The organic salt in the first anode active material layer 22 may be, for example, a compound represented by at least one of Formula 3 or Formula 4:

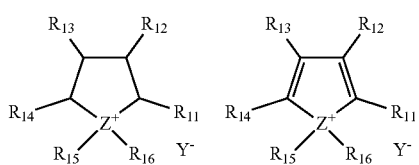

Formula 3

Formula 4

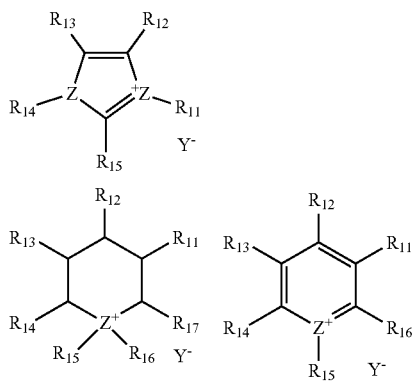

In Formula 3, Z may be N or P, and $R_7$, $R_8$, $R_9$, and $R_{10}$ may be each independently an unsubstituted or halogen-substituted C1-C30 alkyl group, an unsubstituted or halogen-substituted C6-C30 aryl group, an unsubstituted or halogen-substituted C3-C30 heteroaryl group, an unsubstituted or halogen-substituted C4-C30 cycloalkyl group, or an unsubstituted or halogen-substituted C3-C30 heterocycloalkyl group, and $Y^-$ may be an anion.

In Formula 4, Z may be N or P, $R_{11}$, $R_{12}$, $R_{13}$, $R_{14}$, $R_{15}$, $R_{16}$, and $R_{17}$ may be each independently hydrogen, an unsubstituted or halogen-substituted C1-C30 alkyl group, an unsubstituted or halogen-substituted C6-C30 aryl group, an unsubstituted or halogen-substituted C3-C30 heteroaryl group, an unsubstituted or halogen-substituted C4-C30 cycloalkyl group, or an unsubstituted or halogen-substituted C3-C30 heterocycloalkyl group, and $Y^-$ may be an anion.

The organic salt in the first anode active material layer 22 may be, for example, a compound represented by at least one of Formulae 5 to 10:

Formula 5

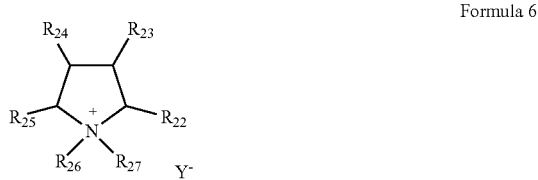

Formula 6

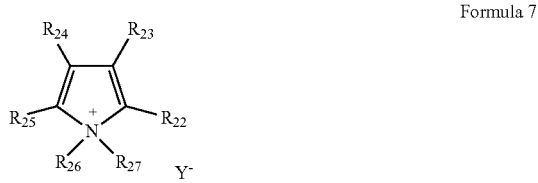

Formula 7

Formula 8

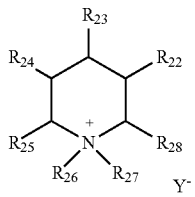

Formula 9

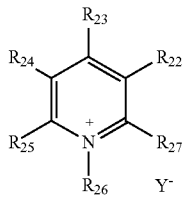

Formula 10

In Formulae 5 to 10, $R_{18}$, $R_{19}$, $R_{20}$, and $R_{21}$ may be each independently an unsubstituted or halogen-substituted C1-C30 alkyl group, an unsubstituted or halogen-substituted C6-C30 aryl group, an unsubstituted or halogen-substituted C3-C30 heteroaryl group, an unsubstituted or halogen-substituted C4-C30 cycloalkyl group, or an unsubstituted or halogen-substituted C3-C30 heterocycloalkyl group, $R_{22}$, $R_{23}$, $R_{24}$, $R_{25}$, $R_{26}$, and $R_{27}$ may be each independently hydrogen, an unsubstituted or halogen-substituted C1-C30 alkyl group, an unsubstituted or halogen-substituted C6-C30 aryl group, an unsubstituted or halogen-substituted C3-C30 heteroaryl group, an unsubstituted or halogen-substituted C4-C30 cycloalkyl group, or an unsubstituted or halogen-substituted C3-C30 heterocycloalkyl group, and $Y^-$ may be an anion.

The organic salt in the first anode active material layer 22 may be, for example, non-volatile. The organic salt may, for example, have a melting point equal to or lower than room temperature, may only be consist of ions, and may be salt in a liquid state at room temperature or a room temperature molten salt. The organic salt may, for example, include at least one of an ammonium cation, a pyrrolidinium cation, a pyridinium cation, a pyrimidinium cation, an imidazolium cation, a piperidinium cation, a pyrazolium cation, an oxazolium cation, a pyridazinium cation, a phosphonium cation, a sulfonium cation, or a triazolium cation; and at least one of $BF_4^-$, $PF_6^-$, $AsF_6^-$, $SbF_6^-$, $AlCl_4^-$, $HSO_4^-$, $ClO_4^-$, $CH_3SO_3^-$, $CF_3CO_2^-$, $Cl^-$, $Br^-$, $I^-$, $BF_4^-$, $SO_4^-$, $CF_3SO_3^-$, $(FSO_2)_2N^-$, $(C_2F_6SO_2)_2N^-$, $(C_2F_5SO_2)(CF_3SO_2)N^-$, or $(CF_3SO_2)_2N^-$. The organic salt may be, for example, at least one of N-methyl-N-propylpyrrolidinium bis(trifluoromethanesulfonyl)imide, N-butyl-N-methylpyrrolidium bis(3-trifluoromethylsulfonyl)imide, 1-butyl-3-methylimidazolium bis(trifluoromethylsulfonyl)amide, or 1-ethyl-3-methylimidazolium bis(trifluoromethylsulfonyl)amide.

Examples of the organic salt in the first anode active material layer 22 may include [emim]Cl/AlCl$_3$ (emim is ethyl methyl imidazolium), [bmpyr]NTf2 (bppyr is butyl methyl pyridinium), [bpy]Br/AlCl$_3$ (bpy is 4,4'-bipyridine), [choline]Cl/CrCl$_3$.6H$_2$O, [Hpy(CH$_2$)$_3$pyH][NTf$_2$]$_2$ (py is pyridinium, NTf is trifluoromethanesulfonimide), [emim] OTf/[hmim]I (hmim is hexyl methyl imidazolium), [choline]Cl/HOCH$_2$CH$_2$OH, [Et$_2$MeN(CH$_2$CH$_2$OMe)]BF$_4$ (Et is ethyl, Me is methyl, Pr is propyl, Bu is butyl, Ph is phenyl, Oct is octyl, Hex is hexyl), [Bu$_3$PCH$_2$CH$_2$C$_8$F$_{17}$]OTf (OTf is trifluoromethane sulfonate), [bmim]PF$_6$ (bmim is butyl methyl imidazolium), [bmim]BF$_4^-$, [omim]PF$_6$ (omim is octyl methyl imidazolium), [Oct$_3$PC$_{18}$H$_{37}$]I, [NC(CH$_2$)$_3$mim]NTf$_2$ (mim is methyl imidazolium), [Pr$_4$N][B(CN)$_4$], [bmim]NTf$_2$, [bmim]Cl, [bmim][Me(OCH$_2$CH$_2$)$_2$OSO$_3$], [PhCH$_2$mim]OTf, [Me$_3$NCH(Me)CH(OH)Ph] NTf$_2$, [pmim][(HO)$_2$PO$_2$] (pmim is propyl methyl imidazolium), [b(6-Me)quin]NTf$_2$ (bquin is butyl quinolinium, [bmim][Cu$_2$Cl$_3$], [C$_{18}$H$_{37}$OCH$_2$mim]BF$_4$ (mim is methyl imidazolium), [heim]PF$_6$ (heim is hexyl ethyl imidazolium), [mim(CH$_2$CH$_2$O)$_2$CH$_2$CH$_2$mim][NTf$_2$]$_2$ (mim is methyl imidazolium), [obim]PF$_6$ (obim is octyl butyl imidazolium), [oquin]NTf$_2$ (oquin is octyl quinolinium), [hmim][PF$_3$(C$_2$F$_5$)$_3$], [C$_{14}$H$_{29}$mim]Br (mim is methyl imidazolium), [Me$_2$N(C$_{12}$H$_{25}$)$_2$]NO$_3$, [emim]BF$_4^-$, [mm(3-NO$_2$)im][dinitrotriazolate] (mm(3-NO$_2$)im is dimethyl-3-NO$_2$-imidazolium), [MeN(CH$_2$CH$_2$OH)$_3$], [MeOSO$_3$], [Hex$_3$PC$_{14}$H$_{29}$]NTf$_2$, [emim][EtOSO$_3$], [choline][ibuprofenate], [emim] NTf$_2$, [emim][(EtO)$_2$PO$_2$], [emim]Cl/CrCl$_2$, or [Hex$_3$PC$_{14}$H$_{29}$]N(CN)$_2$.

A molecular weight of the organic salt represented by at least one of Formulae 1 to 10 in the first anode active material layer 22 may be, for example, in a range of about 50 Dalton to about 1500 Dalton, about 100 Dalton to about 1000 Dalton, about 150 Dalton to about 900 Dalton, about 200 Dalton to about 800 Dalton, or about 250 Dalton to about 700 Dalton. When the organic salt has a molecular weight in these ranges, an ionic conductivity of the organic electrolyte including the organic salt may improve.

In an embodiment, the organic salt in the first anode active material layer 22 may be, for example, an ionic polymer.

The ionic polymer organic salt may be, for example, at least one of a cationic polymer, an anionic polymer, or a zwitterionic polymer.

The cationic polymer is a polymer that includes a cation in a backbone and has an anion as a counter ion.

The cationic polymer may, for example, include a repeating unit including at least one of an ammonium-based cation, a pyrrolidinium-based cation, a pyridinium-based cation, a pyrimidinium-based cation, an imidazolium-based cation, a piperidinium-based cation, a pyrazolium-based cation, an oxazolium-based cation, a pyridazinium-based cation, a phosphonium-based cation, a sulfonium-based cation, or a triazolium-based cation; and at least one of $BF_4^-$—, $PF_6^-$—, $AsF_6^-$—, $SbF_6^-$—, $AlCl_4^-$—, $HSO_4^-$—, $ClO_4^-$—, $CH_3SO_3^-$—, $CF_3CO_2^-$—, $(CF_3SO_2)_2N^-$—, $(FSO_2)_2N^-$—, $Cl^-$—, $Br^-$—, $I^-$—, $SO_4^-$—, $CF_3SO_3^-$—, $(C_2F_5SO_2)_2N^-$—, $(C_2F_5SO_2)(CF_3SO_2)N^-$—, $NO_3^-$—, $Al_2Cl_7^-$—, $(CF_3SO_2)_3C^-$—, $(CF_3)_2PF_4^-$—, $(CF_3)_3PF_3^-$—, $(CF_3)_4PF_2^-$—, $(CF_3)_5PF^-$—, $(CF_3)_6P^-$—, $SF_5CF_2SO_3^-$—, $SF_5CHFCF_2SO_3^-$—, $CF_3CF_2(CF_3)_2CO^-$—, $(CF_3SO_2)_2CH^-$—, $(SF_5)_3C^-$—, or $(O(CF_3)_2C_2(CF_3)_2O)_2PO^-$—.

For example, the cationic polymer may have a structure having at least one of a structure 1 to structure 33.

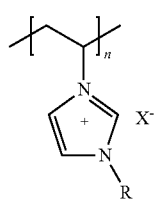

1

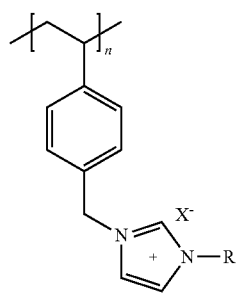
2
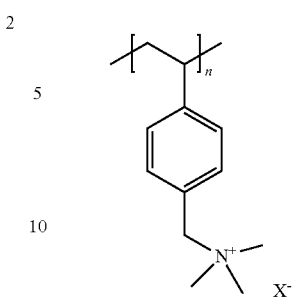
7
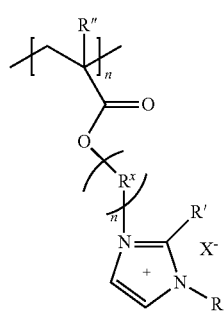
3
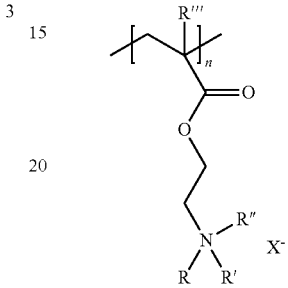
8
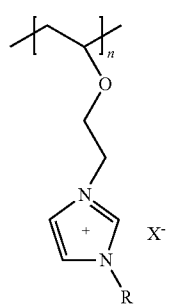
4
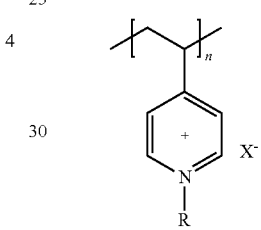
9
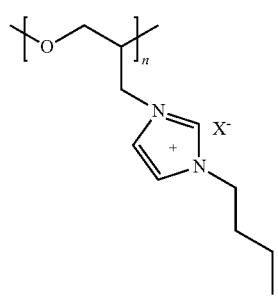
5
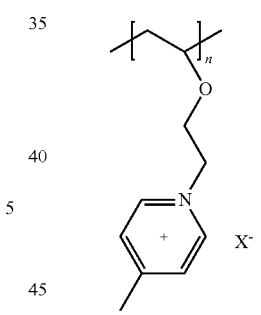
10
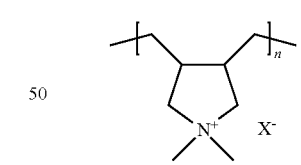
11
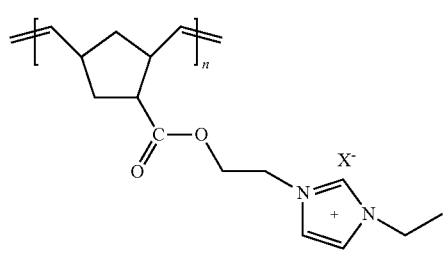
6
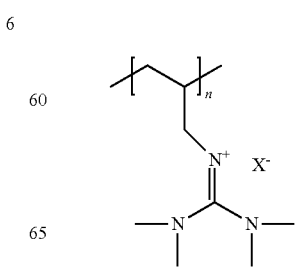
12

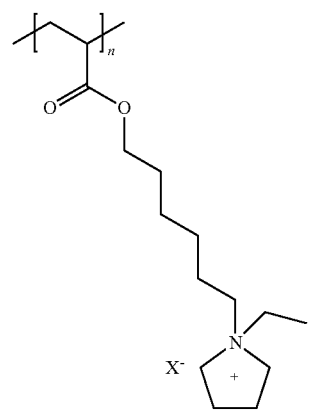
13
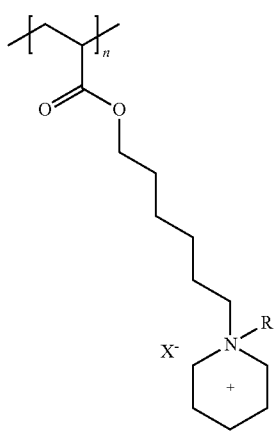
15
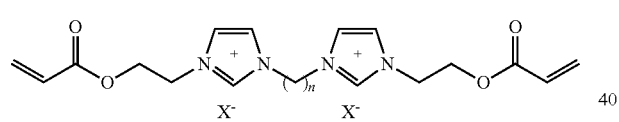
16
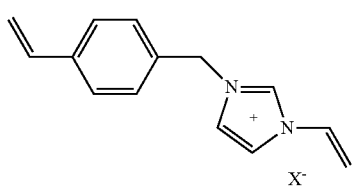
17
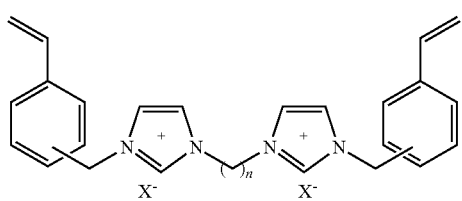
18
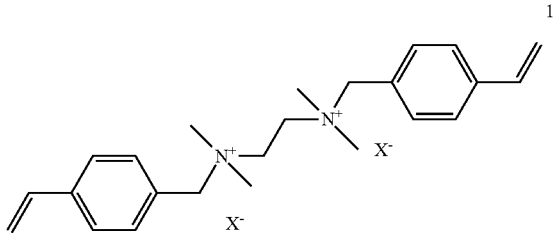
19
20
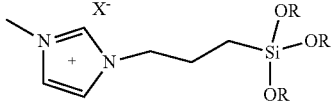
21
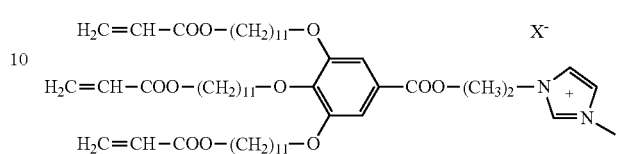
22
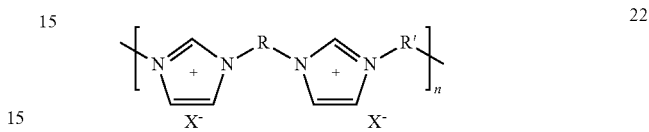
23
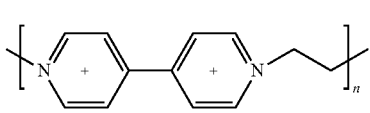
24
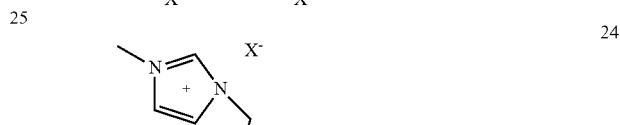
25
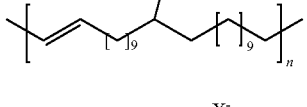
26
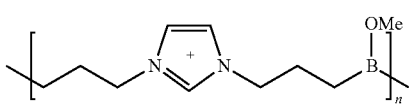
27
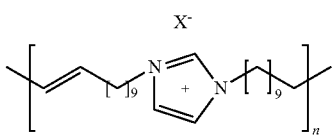
28
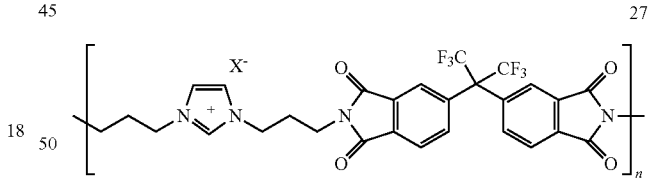
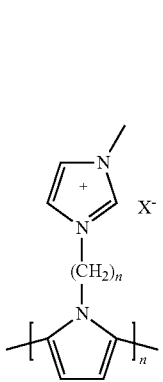

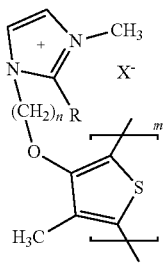
29
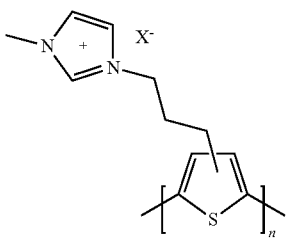
30
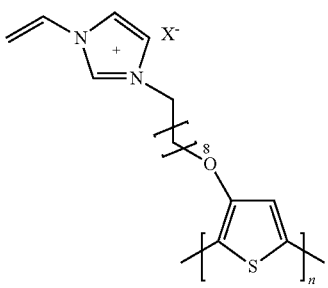
31
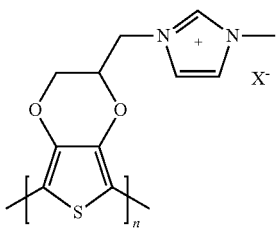
32
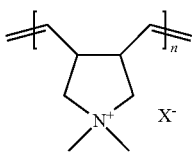
33
R = H, or alkyl  X⁻ = BF₄, PF₆, TFSI, CF₃SO₃•SCN, etc.
The anionic polymer is a polymer that includes an anion in its backbone and has a cation as a counter ion. For example, the anionic polymer may have a structure having at least one of a structure 34 to structure 41.
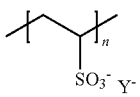
34
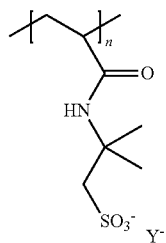
35
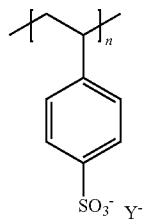
36
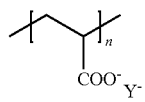
37
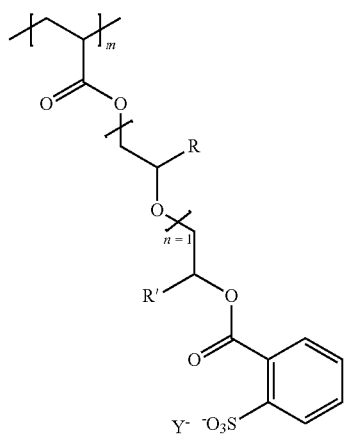
38
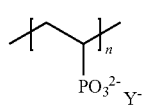
39
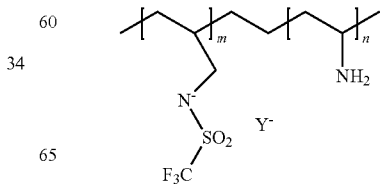
40

41

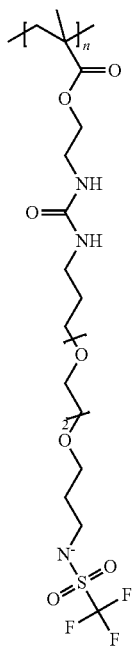

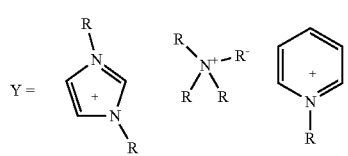

The zwitterionic polymer is a polymer that includes both zwitterions in the backbone and has a cation and/or an anion as a counter ion. For example, the zwitterionic polymer may have a structure having at least one of a structure 42 to structure 47.

42

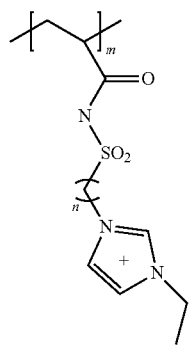

43

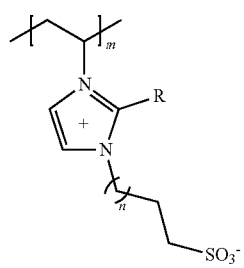

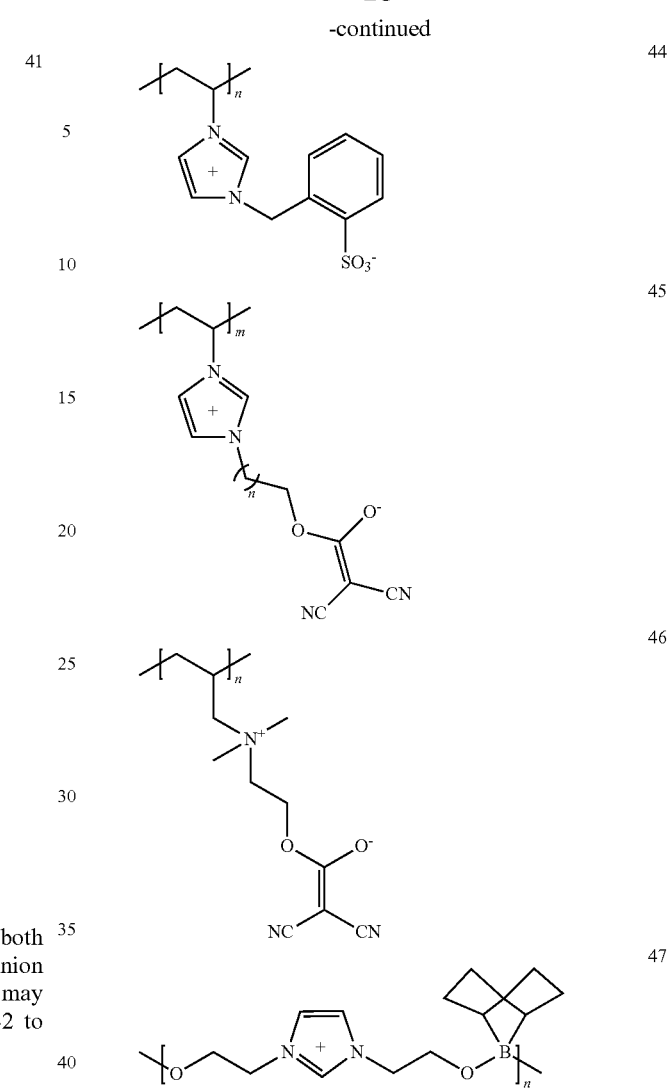

The organic salt in the first anode active material layer 22 may be, for example, a polymer represented by Formula 11:

Formula 11

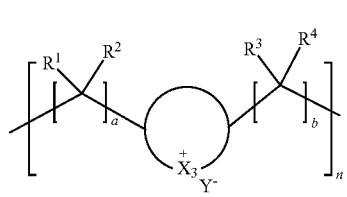

In Formula 11, the structure represented by:

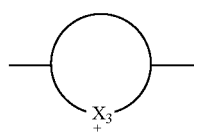

is a heterocycloalkyl or heteroaryl ring including 1 to 3 heteroatoms and 2 to 30 carbon atoms, the ring is unsubstituted or substituted with a substituent group, X is N(R$^5$)(R$^6$)—, —N(R$^5$)=, —P(R$^5$)=, or —P(R$^5$)(R$^6$)—, R$^1$ to R$^6$ are each independently an unsubstituted or halogen-substituted C1-C30 alkyl group, an unsubstituted or halogen-substituted C6-C30 aryl group, an unsubstituted or halogen-substituted C3-C30 heteroaryl group, an unsubstituted or halogen-substituted C4-C30 cycloalkyl group, or an unsubstituted or halogen-substituted C3-C30 heterocycloalkyl group, Y$^-$ is an anion, a and b are each independently an integer of 1 to 5, and n is an integer of 2 to 2800. For example, n may be an integer of 10 to 2800, an integer of 50 to 2700, an integer of 100 to 2600, or an integer of 500 to 2500.

In the organic salt in the first anode active material layer 22, for example, the structure represented by:

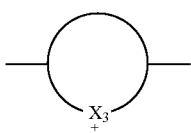

of Formula 11 may be represented by any one of Formula 12:

Formula 12

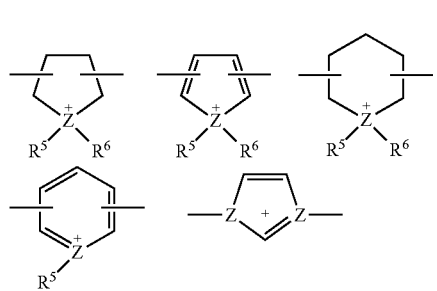

In Formula 12, Z may represent N or P, and R$^5$ and R$^6$ may be each independently an unsubstituted or halogen-substituted C1-C30 alkyl group, an unsubstituted or halogen-substituted C6-C30 aryl group, an unsubstituted or halogen-substituted C3-C30 heteroaryl group, an unsubstituted or halogen-substituted C4-C30 cycloalkyl group, or an unsubstituted or halogen-substituted C3-C30 heterocycloalkyl group.

The organic salt in the first anode active material layer 22 may be, for example, a polymer represented by Formula 13:

Formula 13

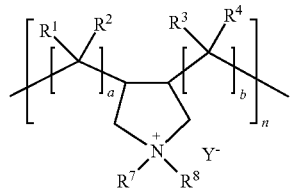

In Formula 13, R$^1$, R$^2$, R$^3$, R$^4$, R$^7$, and R$^8$ are each independently hydrogen, an unsubstituted or substituted C1-C30 alkyl group, an unsubstituted or substituted C1-C30 alkoxy group, an unsubstituted or substituted C6-C30 aryl group, an unsubstituted or substituted C6-C30 aryloxy group, an unsubstituted or substituted C3-C30 heteroaryl group, an unsubstituted or substituted C3-C30 heteroaryloxy group, an unsubstituted or substituted C4-C30 cycloalkyl group, or an unsubstituted or substituted C3-C30 heterocycloalkyl group, or an unsubstituted or substituted C2-Cl0$_0$ alkylene oxide group, Y$^-$ is an anion, a and b are each independently an integer of 1 to 5, and n is an integer of 2 to 2800. For example, n may be an integer of 10 to 2800, an integer of 50 to 2700, an integer of 100 to 2600, or an integer of 500 to 2500.

The organic salt in the first anode active material layer 22 may be, for example, poly(diallyldimethylammonium) bis-trifluoromethanesulfonimide (TFSI).

Examples of the anion of the organic salt in the first anode active material layer 22 may include at least one of BF$_4^-$, PF$_6^-$, AsF$_6^-$, SbF$_6^-$, AlCl$_4^-$, HSO$_4^-$, ClO$_4^-$, CH$_3$SO$_3^-$, CF$_3$CO$_2^-$, Cl$^-$, Br$^-$, I$^-$, BF$_4^-$, SO$_4^-$, PF$_6^-$, ClO$_4^-$, bis(oxalate)borate (BOB$^-$), CF$_3$SO$_3^-$, CF$_3$CO$_2^-$, (C$_2$F$_5$SO$_2$)$_2$N$^-$, (C$_2$F$_5$SO$_2$)(CF$_3$SO$_2$)N$^-$, or (CF$_3$SO$_2$)$_2$N$^-$. For example, the anion in the organic salt represented by at least one of Formulae 1 to 13 may be the same as the anion described above.

A viscosity of the organic salt in the first anode active material layer 22 may be, for example, in a range of about 500 centipoise (cps) to about 10,000 cps, about 600 cps to about 7500 cps, or about 700 cps to about 5000 cps, at a temperature of about 25° C. When a viscosity of the organic salt is within these ranges, the first anode active material layer may easily be molded into various forms. For example, the first anode active material layer 22 may not include an organic solvent.

For example, the organic electrolyte in the first anode active material layer 22 may further include a lithium salt. When the organic electrolyte includes a lithium salt, an ionic conductivity of the organic electrolyte may further improve. The lithium salt may be any suitable lithium salt.

Examples of the lithium salt in the organic electrolyte may include at least one of LiPF$_6^-$, LiBF$_4^-$, LiCF$_3$SO$_3$, Li(CF$_3$SO$_2$)$_2$N, LiC$_2$F$_5$SO$_3$, Li(FSO$_2$)$_2$N, LiC$_4$F$_9$SO$_3$, LiN(SO$_2$CF$_2$CF$_3$)$_2$, of a compound represented by at least one of Formulae 14 to 17.

Formula 14

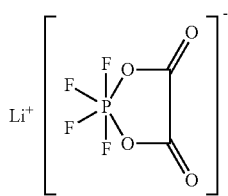

Formula 15

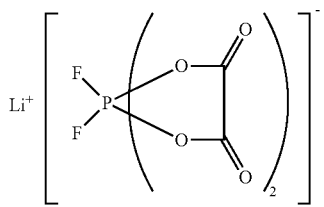

Formula 16

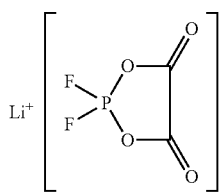

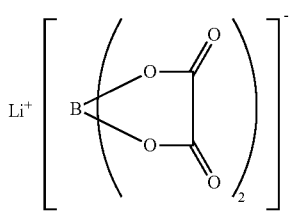

Formula 17

A concentration of the lithium salt in the organic electrolyte may be in a range of about 0.1 moles per liter (molar, M) to about 5 M, about 0.5 M to about 4 M, about 0.55 M to about 3.5 M, about 0.6 M to about 3 M, or about 1 M to about 2.5 M. When a concentration of the lithium salt in the organic electrolyte is within these ranges, deterioration of a lithium battery including the organic electrolyte may be suppressed.

The first anode active material layer 22 may, for example, include the organic electrolyte in a range of about 0.1 parts to about 2.5 parts by weight, about 0.2 parts to about 2.25 parts by weight, about 0.3 parts to about 2.0 parts by weight, about 0.4 parts to about 1.75 parts by weight, about 0.5 parts to about 1.5 parts by weight, or about 0.6 parts to about 1.0 parts by weight, based on 100 parts by weight of the anode active material. When a content of the organic electrolyte is too high, the first anode active material layer 22 and the all-solid secondary battery including the first anode active material layer 22 may not have regular shapes. When a content of the organic electrolyte is too low, an effect of decreasing an interfacial resistance by the organic electrolyte may be insignificant.

The first anode active material layer 22 may, for example, include at least one of a carbon-containing anode active material, a metal anode active material, or a metalloid anode active material.

The metal anode active material or the metalloid anode active material may, for example, have a lithium ion diffusion coefficient higher than a lithium ion diffusion coefficient of lithium metal. When the metal anode active material or the metalloid anode active material has a lithium ion diffusion coefficient higher than that of lithium metal, lithium diffused to the first anode active material layer 22 may rapidly pass through the first anode active material layer 22 and may be induced to be deposited in the form of a uniform lithium metal layer between the first anode active material layer 22 and the anode current collector 21.

For example, the metal or metalloid anode active material may include at least one of indium (In), silicon (Si), gallium (Ga), tin (Sn), aluminum (Al), titanium (Ti), zirconium (Zr), niobium (Nb), germanium (Ge), antimony (Sb), bismuth (Bi), gold (Au), platinum (Pt), palladium (Pd), magnesium (Mg), silver (Ag), and zinc (Zn), but embodiments are not limited thereto, and any suitable metal anode active material or metalloid anode active material capable of forming an alloy or a compound with lithium may be used. For example, nickel (Ni) does not form an alloy with lithium and thus is not a metal anode active material.

The carbon-containing anode active material may be crystalline carbon or amorphous carbon. The crystalline carbon may be, for example, graphite.

The carbon-containing anode active material may be amorphous carbon. Examples of the amorphous carbon may include carbon black (CB), acetylene black (AB), furnace black (FB), Ketjen black (KB), graphene, carbon nanotubes, or carbon fibers, but embodiments are not limited thereto, and any suitable amorphous carbon may be used. The amorphous carbon is carbon having little crystallinity or an exceptionally low crystallinity, which is different from crystalline carbon or graphene-based carbon.

The anode active material in the first anode active material layer 22 may be, for example, in the form of particles. An average particle diameter of the anode active material in the form of particles may be, for example, about 4 μm or less, about 3 μm or less, about 2 μm or less, about 1 μm or less, or about 900 nm or less. An average particle diameter of the anode active material in the form of particles may be, for example, in a range of about 10 nm to about 4 μm or less, about 11 nm to about 3 μm or less, about 12 nm to about 2 μm or less, about 13 nm to about 1 μm or less, or about 14 nm to about 900 nm or less. When the average particle diameter of the anode active material is within these ranges, reversible absorbing and/or desorbing of lithium during charge/discharge may be facilitated. The average particle diameter of the anode active material may be, for example, a median diameter (D50) measured by using a laser diffraction particle diameter distribution meter.

The first anode active material layer 22 may include at least one anode active material or may include a plurality of different anode active materials. For example, the first anode active material layer 22 may only include amorphous carbon or may include at least one of indium (In), silicon (Si), gallium (Ga), tin (Sn), aluminum (Al), titanium (Ti), zirconium (Zr), niobium (Nb), germanium (Ge), antimony (Sb), bismuth (Bi), gold (Au), platinum (Pt), palladium (Pd), magnesium (Mg), silver (Ag), or zinc (Zn). In an embodiment, the first anode active material layer 22 may include a mixture including amorphous carbon and at least one of indium (In), silicon (Si), gallium (Ga), tin (Sn), aluminum (Al), titanium (Ti), zirconium (Zr), niobium (Nb), germanium (Ge), antimony (Sb), bismuth (Bi), gold (Au), platinum (Pt), palladium (Pd), magnesium (Mg), silver (Ag), or zinc (Zn). A mixing ratio of the mixture of amorphous carbon to a metal or metalloid may be a weight ratio in a range of about 10:1 to about 1:2, about 5:1 to about 1:1, or about 4:1 to about 2:1, but embodiments are not limited thereto, and the mixing ratio may be selected according to characteristics of the all-solid secondary battery 1. When the anode active material has the foregoing composition, cycle characteristics of the all-solid secondary battery 1 may improve.

The anode active material in the anode active material layer 22 may include, for example, a mixture including a first particle formed of amorphous carbon and a second particle formed of a metal or a metalloid. Examples of the metal or metalloid may include at least one of indium (In), silicon (Si), gallium (Ga), tin (Sn), aluminum (Al), titanium (Ti), zirconium (Zr), niobium (Nb), germanium (Ge), antimony (Sb), bismuth (Bi), gold (Au), platinum (Pt), palladium (Pd), magnesium (Mg), silver (Ag), or zinc (Zn). In an embodiment, the metalloid may be a semiconductor. An amount of the second particle may be in a range of about 1 weight % to about 60 weight %, about 8 weight % to about 55 weight %, about 10 weight % to about 50 weight %, about 15 weight % to about 40 weight %, or about 20 weight % to about 30 weight %, based on the total weight of the mixture. When the amount of the second particle is within these ranges, for example, cycle characteristics of the all-solid secondary battery 1 may improve.

The first anode active material layer 22 may, for example, further include a binder. Examples of the binder may include at least one of styrene-butadiene rubber (SBR), polytetrafluoroethylene (PTFE), polyvinylidene fluoride (PVDF), polyethylene, a vinylidene fluoride/hexafluoropropylene copolymer, polyacrylonitrile, or polymethylmethacrylate, but embodiments are not limited thereto, and any suitable binder may be used. The binder may be formed of a single binder or a plurality of different binders. The binder may be, for example, an aqueous binder or a non-aqueous binder. The aqueous binder may be dissolved in water or dispersed in water. The non-aqueous binder is dissolved in an organic solvent.

An amount of the organic electrolyte in the first anode active material layer 22 may be in a range of about 1 part by weight to about 50 parts by weight, about 2 parts by weight to about 45 parts by weight, about 3 parts by weight to about 40 parts by weight, about 4 parts by weight to about 30 parts by weight, about 5 parts by weight to about 20 parts by weight, or about 10 parts by weight to about 15 parts by weight, based on 100 parts by weight of the binder. When a content of the organic electrolyte is too high, the first anode active material layer 22 and the all-solid secondary battery 1 including the first anode active material layer 22 may not have regular shapes. When a content of the organic electrolyte is too low, a decrease in interfacial resistance by the organic electrolyte may be insignificant.

When the first anode active material layer 22 includes the binder, the first anode active material layer 22 may be stabilized on the anode current collector 21. Also, cracks of the first anode active material layer 22 may be suppressed despite volume change and/or relative location change of the first anode active material layer 22 during charge/discharge. For example, when the first anode active material layer 22 does not include a binder, the first anode active material layer 22 may be easily separated from the anode current collector 21. As a part of the anode current collector 21 from which the first anode active material layer 22 is detached and is exposed, the exposed part of the anode current collector 21 contacts the solid electrolyte layer 30, and thus a possibility of a short-circuit may increase. The first anode active material layer 22 may be prepared by, for example, coating and drying a slurry, in which materials forming the first anode active material layer 22 are dispersed, on the anode current collector 21. When the binder is included in the first anode active material layer 22, the anode active material may be stably dispersed in the slurry. For example, when the slurry is coated on the anode current collector 21 by using a screen-printing method, clogging of the screen (e.g., clogging by an aggregate of the anode active material) may be suppressed.

A thickness of the first anode active material layer 22 may be, for example, about 50% or less, about 40% or less, about 30% or less, about 20% or less, about 10% or less, or about 5% or less of a thickness of the cathode active material layer 12. For example, a thickness of the first anode active material layer 22 may be in a range of about 1 micrometer (μm) to about 50 μm, about 2 μm to about 40 μm, about 3 μm to about 20 μm, about 4 μm to about 15 μm, about 5 μm to about 10 μm, or about 6 μm to about 9 μm. When the thickness of the first anode active material layer 22 is too thin, lithium dendrites form between the first anode active material layer 22 and the anode current collector 21 destroys the first anode active material layer 22, and thus cycle characteristics of the all-solid secondary battery 1 may not be improved. When the thickness of the first anode active material layer 22 is too thick, an energy density of the all-solid secondary battery 1 may be deteriorated and an oxidation-resistance of the all-solid secondary battery 1 by the first anode active material layer 22 may increase, and thus cycle characteristics of the all-solid secondary battery 1 may not be improved.

An interfacial resistance of the all-solid secondary battery 1 including the first anode active material layer 22 obtained by impedance measurement at 25° C. may be, for example, about 70 (ohm square centimeter) $\Omega \cdot cm^2$ or lower, about 60 $\Omega \cdot cm^2$ or lower, about 50 $\Omega \cdot cm^2$ or lower, about 40 $\Omega \cdot cm^2$ or lower, or about 30 $\Omega \cdot cm^2$ or lower. An interfacial resistance of the all-solid secondary battery 1 including the first anode active material layer 22 obtained by impedance measurement at 25° C. may be, for example, in a range of about 1 $\Omega \cdot cm^2$ to about 70 $\Omega \cdot cm^2$, about 3 $\Omega \cdot cm^2$ to about 60 $\Omega \cdot cm^2$, about 5 $\Omega \cdot cm^2$ to about 50 $\Omega \cdot cm^2$, about 6 $\Omega \cdot cm^2$ to about 40 $\Omega \cdot cm^2$, or about 7 $\Omega \cdot cm^2$ to about 30 $\Omega \cdot cm^2$.

For example, when the thickness of the first anode active material layer 22 decreases, a charge capacity of the first anode active material layer 22 may also decrease. The charge capacity of the first anode active material layer 22 may be, for example, about 50% or lower, about 40% or lower, about 30% or lower, about 20% or lower, about 10% or lower, about 5% or lower, or about 2% or lower of a charge capacity of the cathode active material layer 12. The charge capacity of the first anode active material layer 22 may be, for example, in a range of about 0.1% to about 50%, about 0.2% to about 40%, about 0.3% to about 30%, about 0.4% to about 20%, about 0.5% to about 10%, about 0.6% to about 5%, or about 0.7% to about 2% of a charge capacity of the cathode active material layer 12. When the charge capacity of the first anode active material layer 22 is too low, a thickness of the first anode active material layer 22 is too thin, lithium dendrites form between the first anode active material layer 22 and the anode current collector 21 during repeated charge/discharge processes destroys the first anode active material layer 22, and thus cycle characteristics of the all-solid secondary battery 1 may not be improved. When the charge capacity of the first anode active material layer 22 is too high, an energy density of the all-solid secondary battery 1 may be deteriorated and an internal resistance of the all-solid secondary battery 1 by the first anode active material layer 22 may increase, and thus cycle characteristics of the all-solid secondary battery 1 may not be improved.

The charge capacity of the cathode active material layer 12 may be obtained by multiplying a weight of the cathode active material in the cathode active material layer 12 by a charge capacity density (mAh/g) of the cathode active material. When various types of materials are used as the cathode active material, a value of a charge capacity density times a weight of each of the cathode active materials is calculated, and the total of these values is a charge capacity of the cathode active material layer 12. A charge capacity of the first anode active material layer 22 may be calculated in the same manner. That is, a charge capacity of the first anode active material layer 22 is obtained by multiplying a weight of the anode active material in the first anode active material layer 22 by a charge capacity density (mAh/g) of the anode active material. When various types of materials are used as the anode active material, a value of a charge capacity density times a weight of each of the anode active materials is calculated, and the total of these values is a charge capacity of the first anode active material layer 22. Here, the charge capacity density of the cathode active material and the anode active material is a capacity estimated using an all-solid half-cell in which lithium metal is used as a counter electrode. The charge capacity density of the cathode active material layer 12 and the first anode active material layer 22 are directly measured by charge capacity measurement using an all-solid half-cell. When the measured charge capacity is divided by a weight of each of the active materials, a charge capacity density may be obtained. In an embodiment, the charge capacity of the cathode active material layer 12 and the first anode active material layer 22 may be an initial charge capacity measured in the 1st charge cycle.

The anode current collector 21 may be formed of, for example, a material that does not react with lithium, i.e., a material that does not form both an alloy and a compound. Examples of the material forming the anode current collector 21 may include at least one of copper (Cu), stainless steel, titanium (Ti), iron (Fe), cobalt (Co), or nickel (Ni), but embodiments are not limited thereto, and any suitable electrode current collector may be used. The anode current collector 21 may be formed of a single metal, an alloy, or a covering material of at least two metals. The anode current collector 21 may be, for example, in the form of a plate or a foil.

The first anode active material layer 22 may further include additives that are used in a conventional all-solid secondary battery, such as a filler, a coating agent, a dispersant, or an ion conducting agent.

Referring to FIG. 5, the all-solid secondary battery 1 may further include a thin film 23 including an element capable of capable of forming an alloy with lithium on the anode current collector 21. The thin film 23 may be disposed between the anode current collector 21 and the first anode active material layer 22. The thin film 23 may, for example, include an element capable of forming an alloy with lithium. Examples of the element capable of forming an alloy with lithium may include gold, silver, zinc, tin, indium, silicon, aluminum, and bismuth, but embodiments are not limited thereto, and any suitable element capable of forming an alloy with lithium may be used. The thin film 23 may be formed of any of these metals or alloys of various metals. When the thin film 23 is disposed on the anode current collector 21, for example, the deposition of a second anode active material layer (not shown) deposited between the thin film 23 and the first anode active material layer 22 may further be flattened, and thus cycle characteristics of the all-solid secondary battery 1 may further be improved.

A thickness of the thin film 23 may be, for example, in a range of about 1 nanometer (nm) to about 800 nm, about 10 nm to about 700 nm, about 50 nm to about 600 nm, or about 100 nm to about 500 nm. When the thickness of the thin film 23 is less than 1 nm, the thin film 23 may not be functional. When the thickness of the thin film 23 is too thick, the thin film 23 itself absorbs lithium, and a deposition amount of lithium in an anode may decrease, which results in deterioration of an energy density of the all-solid secondary battery 1, and thus cycle characteristics of the all-solid secondary battery 1 may be deteriorated. The thin film 23 may be disposed on the anode current collector 21 by, for example, vacuum vapor deposition, sputtering, or plating, but embodiments are not limited thereto, and any suitable method capable of forming a thin film may be used. The thin film 23 may be, for example, a plating layer.

Referring to FIG. 6, the all-solid secondary battery 1 may further include, for example, a second anode active material layer 24 disposed between the anode current collector 21 and the first anode active material layer 22. The second anode active material layer 24 may be a metal layer including lithium or a lithium alloy. The metal layer may include lithium or a lithium alloy. Therefore, for example, when the second anode active material layer 24 is a metal layer including lithium, the second anode active material layer 24 may serve as a lithium reservoir. Examples of the lithium alloy may include at least one of a Li—Al alloy, a Li—Sn alloy, a Li—In alloy, a Li—Ag alloy, a Li—Au alloy, a Li—Zn alloy, a Li—Ge alloy, or a Li—Si alloy, but embodiments are not limited thereto, and any suitable lithium alloy may be used. The second anode active material layer 24 may be formed of a single alloy, lithium, or may be formed of various alloys. Although not shown in the drawing, the all-solid secondary battery 1 may further include, for example, a second anode active material layer 24 disposed between the first anode active material layer 22 and the solid electrolyte layer 30.

A thickness of the second anode active material layer 24 may be, for example, in a range of about 1 μm to about 1000 μm, about 2 μm to about 500 μm, about 3 μm to about 200 μm, about 4 μm to about 150 μm, about 5 μm to about 100 μm, or about 6 μm to about 50 μm, but embodiments are not limited thereto. When the thickness of the second anode active material layer 24 is too thin, the second anode active material layer 24 may not serve as a lithium reservoir. When the thickness of the second anode active material layer 24 is too thick, a weight and a volume of the all-solid secondary battery 1 may increase, and cycle characteristics may be deteriorated. The second anode active material layer 24 may be, for example, a metal foil having a thickness in these ranges.

In the all-solid secondary battery 1, the second anode active material layer 24 may be disposed between the anode current collector 21 and the first anode active material layer 22 before assembling the all-solid secondary battery 1. In an embodiment, the second anode active material layer 24 in the all-solid secondary battery 1 may be, for example, deposited between the anode current collector 21 and the first anode active material layer 22 by charging after assembling the all-solid secondary battery 1.

When the second anode active material layer 24 is disposed between the anode current collector 21 and the first anode active material layer 22 before assembling the all-solid secondary battery 1, the second anode active material layer 24 is a metal layer including lithium and thus may serve as a lithium reservoir. Cycle characteristics of the all-solid secondary battery 1 including the second anode active material layer 24 may further be improved. For example, a lithium foil may be disposed between the anode current collector 21 and the first anode active material layer 22 or between the first anode active material layer 22 and the solid electrolyte layer 30 before assembling the all-solid secondary battery 1.

When the second anode active material layer 24 is disposed by charging after assembling the all-solid secondary battery 1, an energy density of the all-solid secondary battery 1 increases due to not including the second anode active material layer 24 during the assembling of the all-solid secondary battery 1. For example, the all-solid secondary battery 1 may be charged over a charge capacity of the first anode active material layer 22. That is, the first anode active material layer 22 may be overcharged. In the beginning of the charge, lithium is absorbed and/or deposited in the first anode active material layer 22. That is, the anode active material in the first anode active material layer 22 may form an alloy or a compound with lithium ions migrated from the cathode layer 10. When the anode active material layer is charged over the charge capacity of the first anode active material layer 22, for example, lithium is deposited on a back surface of the first anode active material layer 22, which is between the anode current collector 21 and the first anode active material layer 22, and a metal layer corresponding to the second anode active material layer 24 may be formed by the deposited lithium. The second anode active material layer 24 is a metal layer including b mainly formed of lithium (i.e., metal lithium). This happens because, for example, the anode active material in the first anode active material layer 22 is formed of a material capable of forming an alloy or a compound with lithium. During discharge, lithium of the first anode active material layer 22 and the second anode active material layer 24, that is a metal layer, is ionized and migrates in a direction towards the cathode layer 10. Thus, lithium may be used as an anode active material in the all-solid secondary battery 1. Also, when the first anode active material layer 22 covers the second anode active material layer 24, the first anode active material layer 22 serves as a protection layer of the second anode active material layer 24 and suppresses deposition growth of lithium dendrite at the same time. Thus, short-circuit and capacity deterioration of the all-solid secondary battery 1 may be suppressed, and, as a result, cycle characteristics of the all-solid secondary battery 1 may be improved. Also, when the second anode active material layer 24 is formed by charging after the assembling of the all-solid secondary battery 1, a region between the anode current collector 21 and the first anode active material layer 22 may be, for example, a Li-free region substantially not including lithium (Li) in the initial state or a state after the discharge of the all-solid secondary battery 1.

Solid Electrolyte Layer

Referring to FIGS. 1 to 4, the solid electrolyte layer 30 may be disposed between the cathode layer 10 and the anode layer 20 and may include a solid electrolyte.

The solid electrolyte in the solid electrolyte layer 30 may be, for example, an inorganic solid electrolyte. For example, the solid electrolyte layer 30 may not include a polymer solid electrolyte. The solid electrolyte in the solid electrolyte layer 30 may be, for example, at least one of a sulfide-containing solid electrolyte or an oxide-containing solid electrolyte.

The solid electrolyte may be, for example, an oxide-containing solid electrolyte. Examples of the oxide-containing solid electrolyte may include at least one of $Li_{1+x+y}Al_xTi_{2-x}Si_yP_{3-y}O_{12}$ (where $0<x<2$ and $0\le y<3$), $BaTiO_3$, $Pb(Zr_aTi_{1-a})O_3$ (PZT) (where $0\le a\le 1$), $Pb_{1-x}La_xZr_{1-y}Ti_yO_3$ (PLZT) (where $0\le x<1$ and $0\le y\le 1$), $PB(Mg_{1/3}Nb_{2/3})O_3$—$PbTiO_3$ (PMN-PT), $HfO_2$, $SrTiO_3$, $SnO_2$, $CeO_2$, $Na_2O$, $MgO$, $NiO$, $CaO$, $BaO$, $ZnO$, $ZrO_2$, $Y_2O_3$, $Al_2O_3$, $TiO_2$, $SiO_2$, $Li_3PO_4^-$, $Li_xTi_y(PO_4)_3$ (where $0<x<2$ and $0<y<3$), $Li_xAl_yTi_z(PO_4)_3$ (where $0<x<2$, $0<y<1$, and $0<z<3$), $Li_{1+x+y}(Al_aGa_{1-a})_x(Ti_bGe_{1-b})_{2-x}Si_yP_{3-y}O_{12}$ (where $0\le x\le 1$, $0\le y\le 1$, $0\le a\le 1$, and $0\le b\le 1$), $Li_xLa_yTiO_3$ (where $0<x<2$ and $0<y<3$), $Li_2O$, $LiOH$, $Li_2CO_3$, $LiAlO_2$, $Li_2O$—$Al_2O_3$—$SiO_2$—$P_2O_5$—$TiO_2$—$GeO_2$, and $Li_{3+x}La_3M_2O_{12}$ (where M is Te, Nb, or Zr, and $0\le x\le 10$). The solid electrolyte may be prepared using a sintering method.

The oxide-containing solid electrolyte may be, for example, a Garnet-type solid electrolyte of $Li_7La_3Zr_2O_{12}$ (LLZO) or $Li_{3+x}La_3Zr_{2-a}M_aO_{12}$ (M-doped LLZO, where M is Ga, W, Nb, Ta, or Al, and $0\le x\le 10$).

In an embodiment, the solid electrolyte may be, for example, a sulfide-containing solid electrolyte. Examples of the sulfide-containing solid electrolyte may include at least one of $Li_2S$—$P_2S_5$, $Li_2S$—$P_2S_5$—$LiX$ (where X is a halogen element), $Li_2S$—$P_2S_5$—$Li_2O$, $Li_2S$—$P_2S_5$—$Li_2O$—$LiI$, $Li_2S$—$SiS_2$, $Li_2S$—$P_2S_5$—$LiI$, $Li_2S$—$SiS_2$—$LiBr$, $Li_2S$—$SiS_2$—$LiCl$, $Li_2S$—$SiS_2$—$B_2S_3$—$LiI$, $Li_2S$—$SiS_2$—$P_2S_5$—$LiI$, $Li_2S$—$B_2S_3$, $Li_2S$—$P_2S_5$—$Z_mS_n$ (where m and n each are a positive number, Z represents any of Ge, Zn, and Ga), $Li_2S$—$GeS_2$, $Li_2S$—$SiS_2$—$Li_3PO_4^-$, $Li_2S$—$SiS_2$—$Li_pMO_q$ (where p and q each are a positive number, M represents at least one of P, Si, Ge, B, Al, Ga, or In), $Li_{7-x}PS_{6-x}Cl_x$ (where $0\le x\le 2$), $Li_{7-x}PS_{6-x}Br_x$ (where $0\le x\le 2$), or $Li_{7-x}PS_{6-x}I_x$ (where $0\le x\le 2$). The sulfide-containing solid electrolyte may be prepared by melting and quenching starting materials (e.g., $Li_2S$ or $P_2S_5$), or mechanical milling the starting materials. Subsequently, the resultant may be heat-treated. The sulfide-containing solid electrolyte may be amorphous or crystalline and may be a mixed form thereof.

Also, the sulfide-containing solid electrolyte may include at least sulfur (S), phosphorus (P), and lithium (Li), as component elements among the sulfide-containing solid electrolyte materials. For example, the sulfide-containing solid electrolyte may be a material including $Li_2S$—$P_2S_5$. Here, when the material including $Li_2S$—$P_2S_5$ is used as a sulfide-containing solid electrolyte material, a mixing molar ratio of $Li_2S$ and $P_2S_5$ ($Li_2S:P_2S_5$) may be, for example, selected in a range of about 50:50 to about 90:10.

For example, the sulfide-containing solid electrolyte may include an argyrodite-type solid electrolyte represented by Formula 18:

$$Li^+{}_{12-n-x}A^{n+}X^{2-}{}_{6-x}Y^-{}_x \qquad \text{Formula 18}$$

In Formula 18, A is at least one of P, As, Ge, Ga, Sb, Si, Sn, Al, In, Ti, V, Nb, or Ta, X is at least one of S, Se, or Te, Y is at least one of Cl, Br, I, F, CN, OCN, SCN, or $N_3$, $1\le n\le 5$, and $0\le x\le 2$.

The sulfide-containing solid electrolyte may be an argyrodite-type compound including at least one of $Li_{7-x}PS_{6-x}Cl_x$ (where $0\le x\le 2$), $Li_{7-x}PS_{6-x}Br_x$ (where $0\le x\le 2$), or $Li_{7-x}PS_{6-x}I_x$ (where $0\le x\le 2$). Particularly, the sulfide-containing solid electrolyte in the solid electrolyte layer 30 may be an argyrodite-type compound including at least one of $Li_6PS_5Cl$, $Li_6PS_5Br$, or $Li_6PS_5I$.

The solid electrolyte layer 30 may, for example, include a binder. Examples of the binder in the solid electrolyte layer 30 may include styrene butadiene rubber (SBR), polytetrafluoroethylene, polyvinylidene fluoride, or polyethylene, but embodiments are not limited thereto, and any suitable binder may be used. The binder of the solid electrolyte 30 may be the same as or different from a binder of the cathode active material layer 12 and the first anode active material layer 22.

Cathode Layer

The cathode layer 10 may include the cathode current collector 11 and the cathode active material layer 12.

The cathode current collector 11 may use, for example, a plate or foil comprising at least one of indium (In), copper (Cu), magnesium (Mg), stainless steel, titanium (Ti), iron (Fe), cobalt (Co), nickel (Ni), zinc (Zn), aluminum (Al), germanium (Ge), lithium (Li), or an alloy thereof. The cathode current collector 11 may be omitted.

The cathode active material layer 12 may include, for example, a cathode active material.

The cathode active material may be a cathode active material capable of reversely absorbing and desorbing lithium ions. Examples of the cathode active material may include a lithium transition metal oxide such as a lithium cobalt oxide (LCO), a lithium nickel oxide, a lithium nickel cobalt oxide, a lithium nickel cobalt aluminum oxide (NCA), a lithium nickel cobalt manganese oxide (NCM), a lithium manganate, or a lithium iron phosphate; a nickel sulfide; a copper sulfide; a lithium sulfide; an iron oxide; or a vanadium oxide, but embodiments are not limited thereto, and any suitable cathode active material may be used. The cathode active material may be used alone or in a mixture of at least two cathode active materials.

The lithium transition metal oxide may be, for example, a compound represented by at least one of $Li_aA_{1-b}B'_bD_2$ (where $0.90 \leq a \leq 1$ and $0 \leq b \leq 0.5$); $Li_aE_{1-b}B'_bO_{2-c}D_c$ (where $0.90 \leq a \leq 1$, $0 \leq b \leq 0.5$, and $0 \leq c \leq 0.05$); $LiE_{2-b}B'_bO_{4-c}D_c$ (where $0 \leq b \leq 0.5$ and $0 \leq c \leq 0.05$); $Li_aNi_{1-b-c}Co_bB'_cD_\alpha$ (where $0.90 \leq a \leq 1$, $0 \leq b \leq 0.5$, $0 \leq c \leq 0.05$, and $0 < \alpha \leq 2$); $Li_aNi_{1-b-c}Co_bB'_cO_{2-\alpha}F'_\alpha$ (where $0.90 \leq a \leq 1$, $0 \leq b \leq 0.5$, $0 \leq c \leq 0.05$, and $0 < \alpha < 2$); $Li_aNi_{1-b-c}Co_bB'_cO_{2-\alpha}F'_2$ (where $0.90 \leq a \leq 1$, $0 \leq b \leq 0.5$, $0 \leq c \leq 0.05$, and $0 < \alpha < 2$); $Li_aNi_{1-b-c}Mn_bB'_cD_\alpha$ (where $0.90 \leq a \leq 1$, $0 \leq b \leq 0.5$, $0 \leq c \leq 0.05$, and $0 < \alpha \leq 2$); $Li_aNi_{1-b-c}Mn_bB'_cO_{2-\alpha}F'_\alpha$ (where $0.90 \leq a \leq 1$, $0 \leq b \leq 0.5$, $0 \leq c \leq 0.05$, and $0 < \alpha < 2$); $Li_aNi_{1-b-c}Mn_bB'_cO_{2-\alpha}F'_2$ (where $0.90 \leq a \leq 1$, $0 \leq b \leq 0.5$, $0 \leq c \leq 0.05$, and $0 < \alpha < 2$); $Li_aN-i_bE_cG_dO_2$ (where $0.90 \leq a \leq 1$, $0 \leq b \leq 0.9$, $0 \leq c \leq 0.5$, and $0.001 \leq d \leq 0.1$); $Li_aNi_bCo_cMn_dGeO_2$ (where $0.90 \leq a \leq 1$, $0 \leq b \leq 0.9$, $0 \leq c \leq 0.5$, $0 \leq d \leq 0.5$, and $0.001 \leq e \leq 0.1$); $Li_aNiG_bO_2$ (where $0.90 \leq a \leq 1$ and $0.001 \leq b \leq 0.1$); $Li_aCoG_bO_2$ (where $0.90 \leq a \leq 1$ and $0.001 \leq b \leq 0.1$); $Li_aMnG_bO_2$ (where $0.90 \leq a \leq 1$ and $0.001 \leq b \leq 0.1$); $Li_aMn_2GbO_4$ (where $0.90 \leq a \leq 1$ and $0.001 \leq b \leq 0.1$); $QO_2$; $QS_2$; $LiQS_2$; $V_2O_5$; $LiV_2O_5$; $LiI'O_2$; $LiNiVO_4$; $Li_{(3-f)}J_2(PO_4)_3$ (where $0 \leq f \leq 2$); $Li_{(3-f)}Fe_2(PO_4)_3$ (where $0 \leq f \leq 2$); and $LiFePO_4$. In the compound, A may be nickel (Ni), cobalt (Co), manganese (Mn), or a combination thereof; B' may be aluminum (Al), nickel (Ni), cobalt (Co), manganese (Mn), chromium (Cr), iron (Fe), magnesium (Mg), strontium (Sr), vanadium (V), a rare earth element, or a combination thereof; D may be oxygen (O), fluorine (F), sulfur (S), phosphorus (P), or a combination thereof; E may be cobalt (Co), manganese (Mn), or a combination thereof; F' may be fluorine (F), sulfur (S), phosphorus (P), or a combination thereof; G may be (Al), chromium (Cr), manganese (Mn), iron (Fe), magnesium (Mg), lanthanum (La), cerium (Ce), strontium (Sr), vanadium (V), or a combination thereof; Q may be titanium (Ti), molybdenum (Mo), manganese (Mn), or a combination thereof; I' may be chromium (Cr), vanadium (V), iron (Fe), scandium (Sc), yttrium (Y), or a combination thereof; and J may be vanadium (V), chromium (Cr), manganese (Mn), cobalt (Co), nickel (Ni), copper (Cu), or a combination thereof. The compounds may have a surface coating layer (hereinafter, also referred to as "coating layer"). Alternatively, a mixture of a compound without a coating layer and a compound having a coating layer, the compounds being selected from the compounds listed above, may be used. In an embodiment, the coating layer may include at least one compound of a coating element selected from the group consisting of oxide, hydroxide, oxyhydroxide, oxycarbonate, and hydroxycarbonate of the coating element. In an embodiment, the compounds for the coating layer may be amorphous or crystalline. In an embodiment, the coating element for the coating layer may be magnesium (Mg), aluminum (Al), cobalt (Co), potassium (K), sodium (Na), calcium (Ca), silicon (Si), titanium (Ti), vanadium (V), tin (Sn), germanium (Ge), gallium (Ga), boron (B), arsenic (As), zirconium (Zr), or a mixture thereof. In an embodiment, the coating layer may be formed using any method that does not adversely affect the physical properties of the cathode active material when a compound of the coating element is used. For example, the coating layer may be formed using a spray coating method or a dipping method. The coating method may be well understood by one of ordinary skill in the art, and thus a detailed description thereof will be omitted.

The cathode active material may include, for example, a lithium salt of a transition metal oxide that has a layered rock-salt type structure among the examples of the lithium transition metal oxide. For example, the "layered rock-salt type structure" refers to a structure in which an oxygen atom layer and a metal atom layer are alternately and regularly arranged in a <111> direction in a cubic rock-salt type structure, where each of the atom layers forms a two-dimensional flat plane. The "cubic rock-salt type structure" refers to a sodium chloride (NaCl) type structure, which is one of the crystalline structures, in particular, to a structure in which face-centered cubic (fcc) lattices respectively formed of anions and cations are shifted by only a half of the ridge of each unit lattice. Examples of the lithium transition metal oxide having the layered rock-salt type structure may include a ternary lithium transition metal oxide expressed as $LiNi_xCo_yAl_zO_2$ (NCA) or $LiNi_xCo_yMn_zO_2$ (NCM) (where $0 < x < 1$, $0 < y < 1$, $0 < z < 1$, and $x + y + z = 1$). When the cathode active material includes a ternary transition metal oxide having the layered rock-salt type structure, an energy density and thermal stability of the all-solid secondary battery 1 may be improved.

A coating layer may cover the cathode active material as described above. The coating layer is any material that may be used as a coating layer of a cathode active material of an all-solid secondary battery in the art. The coating layer may be, for example, $Li_2O$—$ZrO_2$.

When the cathode active material includes nickel (Ni) as a ternary lithium transition metal oxide such as NCA or NCM, a capacity density of the all-solid secondary battery 1 increases, and thus metal elution from the cathode active material in a charged state may be reduced. As a result, the all-solid secondary battery 1 according to an embodiment may have improved cycle characteristics in a charged state.

A shape of the cathode active material may be, for example, particle shapes such as a true spherical shape, an elliptical shape, or a spherical shape. A particle diameter of the cathode active material is not particularly limited but may be in a range applicable to a cathode active material of a conventional all-solid secondary battery. An amount of the cathode active material of the cathode layer 10 is not particularly limited and may be in a range applicable to a cathode layer of a conventional all-solid secondary battery.

Additives such as a conducting agent, a binder, a filler, a dispersant, and an ion conducting agent may be added to the cathode layer 10 in addition to the cathode active material. Examples of the conducting agent may include graphite, carbon black, acetylene black, Ketjen black, carbon fiber, or metal powder. Examples of the binder may include styrene butadiene rubber (SBR), polytetrafluoroethylene, polyvinylidene fluoride, or polyethylene. The coating agent, the dispersant, and the ion conducting agent that may be added to the cathode layer 10 may be any suitable materials for an electrode of an all-solid secondary battery.

The cathode layer 10 may further include a solid electrolyte. The solid electrolyte in the cathode layer 10 may be similar to or different from a solid electrolyte in the solid electrolyte layer 30. Details of the solid electrolyte are the same as defined with reference to the solid electrolyte layer 30.

In an embodiment, the cathode layer 10 may further include, for example, an organic electrolyte. Details of the organic electrolyte are the same as defined with reference to the anode layer 20. An amount of the organic electrolyte in the cathode layer 10 may be, for example, in a range of about 0 parts by weight to about 50 parts by weight, about 1 part by weight to about 30 parts by weight, about 2 parts by weight to about 20 parts by weight, about 3 parts by weight to about 10 parts by weight, or about 4 parts by weight to about 8 parts by weight based on 100 parts by weight of the cathode active material 12.

According to an embodiment, a method of preparing the all-solid secondary battery 1 may include providing a first anode active material layer including an anode active material and an organic electrolyte capable of forming an alloy or a compound with lithium; arranging the first anode active material layer on a solid electrolyte layer or a second anode active material layer to prepare a first stack; arranging the second anode active material layer or solid electrolyte layer on the first anode active material layer to prepare a second stack; and pressing the first stack and the second stack together to form the all-solid secondary battery, wherein the organic electrolyte includes an organic salt containing an organic cation and an anion.

When an all-solid secondary battery 1 is prepared in this manner, the occurrence of a short-circuit at a high-current density is suppressed, and thus the all-solid secondary battery 1 having excellent lifespan characteristics and an improved energy density may be provided.

In an embodiment, a method of preparing the all-solid secondary battery 1 may, for example, include providing a first anode active material layer including an anode active material and an organic electrolyte capable of forming an alloy or a compound with lithium; arranging the first anode active material layer on a solid electrolyte layer to prepare a first stack; arranging a second anode active material layer on the first anode active material layer to prepare a second stack; and arranging a cathode layer on the solid electrolyte layer of the second stack. That is, the first anode active material layer may first be disposed on the solid electrolyte layer, and then the second anode active material layer may be disposed on the first anode active material layer.

In an embodiment, a method of preparing the all-solid secondary battery 1 may, for example, include providing a first anode active material layer including an anode active material and an organic electrolyte capable of forming an alloy or a compound with lithium; arranging the first anode active material layer on a second anode active material layer to prepare a first stack; arranging a solid electrolyte layer on the first anode active material layer to prepare a second stack; and arranging a cathode layer on the solid electrolyte layer of the second stack. That is, the first anode active material layer may first be disposed on the second anode active material layer, and then the solid electrolyte layer may be disposed on the first anode active material layer.

The all-solid secondary battery 1 may be prepared by, for example, first separately preparing the cathode layer 10, the anode layer 20, and the solid electrolyte layer 30 and then stacking these layers.

Preparation of Cathode Active Material Layer

Materials constituting the cathode active material layer 12 such as a cathode active material, a carbon-containing conducting agent, a hybrid electrolyte may be mixed to prepare a slurry. The slurry may be coated and dried on a cathode current collector 11 to prepare a stack. The obtained stack may be pressed to prepare a cathode layer 10. The pressing process may be performed by, for example, roll pressing, flat pressing, or isotactic pressing, but embodiments are not limited thereto, and any suitable pressing method may be used. The pressing process may be omitted. A mixture of the materials constituting the cathode active material layer 12 may be compressed into the form of a pellet or stretched (molded) in the form of sheet to prepare the cathode layer 10. When the cathode layer 10 is prepared in this manner, the cathode current collector 11 may be omitted.

Preparation of Anode Active Material Layers

Materials comprising a first anode active material layer 22 such as an anode active material, an organic electrolyte, optionally a conducting agent, and optionally a binder may be added to a polar solvent or a non-polar solvent to prepare a slurry. The slurry may be coated and dried on a releasable substrate, e.g., a stainless steel (SUS) substrate, to dispose the first anode active material layer on the releasable substrate, and this may be pressed to prepare a releasable substrate/first anode active material layer 22 stack. The pressing process may be performed by, for example, roll pressing, flat pressing, or isotactic pressing, but embodiments are not limited thereto, and any pressing method available in the art may be used. The pressing process may be performed, for example, at a temperature in a range of room temperature to about 90° C. or lower or about 20° C. to about 90° C. In an embodiment, the pressing process may be performed at a high temperature of about 100° C. or higher. The pressing process may be omitted.

Also, a second anode active material layer 24, which is a lithium metal layer, may be disposed on an anode current collector 21 to prepare an anode current collector 21/second anode active material layer 24 stack. The releasable substrate/first anode active material layer 22 stack may be disposed on the anode current collector 21/second anode active material layer 24 stack such that the first anode active material layer 22 contacts the lithium metal layer, and the resultant may be pressed to prepare a pressed third stack. The pressing process may be performed by, for example, cold isostatic pressing (CIP). A pressing temperature may be room temperature. The pressing temperature may be, for example, about 40° C. or lower or about 30° C. or lower. The pressing temperature may be, for example, about 25° C. A pressure of the pressing process may be about 400 MPa or lower, about 350 MPa or lower, about 300 MPa or lower, or about 250 MPa or lower. A pressure of the pressing process may be in a range of about 1 MPa to about 400 MPa, about 10 MPa to about 390 MPa, about 100 MPa to about 380 MPa, about 110 MPa to about 350 MPa, about 120 MPa to about 300 MPa, or about 130 MPa to about 250 MPa. The releasable substrate may be removed from the third stack to prepare an anode layer 20 in which the anode current collector 21/second anode active material layer 24/first anode active material layer 22 are stacked.

In an embodiment, the second anode active material layer 24 may be omitted in the preparation of the anode layer 20 and may be formed by deposition on the anode current collector 21 by charging after preparation of the all-solid secondary battery 1.

Preparation of Solid Electrolyte Layer

For example, a solid electrolyte layer 30 including an oxide-containing solid electrolyte may be prepared by heat-treating a precursor of an oxide-containing solid electrolyte material.

The oxide-containing solid electrolyte may be prepared by contacting the precursors at a desired stoichiometric amount to form a mixture, and then heat-treating the mixture. The contacting may be, for example, performed by milling such as ball milling or pulverization. The mixture of the precursors mixed in stoichiometric amounts is primarily heat-treated in an oxidative atmosphere to prepare a primary heat-treatment resultant. The primary heat-treatment may be performed at a temperature lower than about 1000° C. for about 1 hour to about 36 hours. The primary heat-treatment temperature may be about 20° C. to about 1000° C., about 30° C. to about 900° C., about 40° C. to about 800° C., about 50° C. to about 700° C., or about 60° C. to about 600° C. The primary heat-treatment time may be about 1 hour to about 36 hours, 4 hours to about 30 hours, 8 hours to about 24 hours, or 12 hours to about 18 hours.

The primary heat-treatment resultant may be pulverized. The pulverizing of the primary heat-treatment may be dry pulverizing or wet pulverizing. For example, the wet pulverizing may be performed by mixing a solvent such as methanol and the primary heat-treatment resultant, and milling the mixture using a ball mill for about 0.5 hours to about 10 hours. The dry pulverizing may be performed by milling the resultant using a ball mill without a solvent. A particle diameter of the primary heat-treatment resultant may be in a range of about 0.1 µm to about 10 µm or about 0.2 µm to about 5 µm. The pulverized primary heat-treatment resultant may be dried. The pulverized primary heat-treatment resultant is mixed with a binder solution and molded in the form of a pellet or may be simply pressed at a pressure of about 1 ton to about 10 tons, or about 3 tons to about 7 tons, to be molded in the form of a pellet.

The molded result may be secondarily heat-treated at a temperature lower than about 1000° C. for about 1 hour to about 36 hours. From the second heat-treatment, a solid electrolyte layer 30 is obtained as a sintered resultant. The secondary heat-treatment may be performed at a temperature, for example, in a range of about 550° C. to about 1000° C. The secondary heat-treatment may be performed for about 1 hour to about 36 hours. The secondary heat-treatment time may be about 1 hour to about 36 hours, 4 hours to about 30 hours, 8 hours to about 24 hours, or 12 hours to about 18 hours. A temperature of the secondary heat-treatment is higher than the temperature of the primary heat-treatment to obtain the sintered resultant. For example, the temperature of the secondary heat-treatment is about 10° C. or more, about 20° C. or more, about 30° C. or more, or about 50° C. or more than that of the primary heat-treatment temperature. The molded result may be secondarily heat-treated in at least one of an oxidative atmosphere or a reductive atmosphere. The secondary heat-treatment may be performed in an oxidative atmosphere, a reductive atmosphere, or an oxidative atmosphere and a reductive atmosphere.

For example, the solid electrolyte layer 30 including a sulfide-containing solid electrolyte may be prepared by using a solid electrolyte formed of sulfide-containing solid electrolyte materials.

The sulfide-containing solid electrolyte may be prepared by treating starting materials with a melt quenching method or a mechanical milling method, but embodiments are not limited thereto, and any suitable method of preparing a sulfide-containing solid electrolyte may be used. For example, when the sulfide-containing solid electrolyte is prepared by using a melt quenching method, predetermined amounts of the starting materials, $Li_2S$ and $P_2S_5$, are mixed into a pellet phase, reacted at a predetermined reaction temperature in vacuum, and quenched to obtain a sulfide-containing solid electrolyte. Also, the reaction temperature of the mixture of $Li_2S$ and $P_2S_5$ may be, for example, in a range of about 400° C. to about 1000° C., about 500° C. to about 950° C., or about 800° C. to about 900° C. A period of time for the reaction may be in a range of about 0.1 hours to about 12 hours, or, for example, about 1 hour to about 12 hours. A temperature of the quenching may be, for example, about 10° C. or lower, or, for example, about 0° C. or lower, and a rate of the quenching may be in a range of, for example, 1° C./sec to about 10000° C./sec, or, for example, about 1° C./sec to about 1000° C./sec. For example, when the sulfide-containing solid electrolyte is prepared by using a mechanical milling method, the starting materials, $Li_2S$ and $P_2S_5$, are mixed and reacted by stirring the mixture using a ball mill to obtain a sulfide-containing solid electrolyte. A rate and a period of time of stirring of the mechanical milling method are not particularly limited, but, when the rate of stirring is high, a production rate of the solid electrolyte increases, and, when the period of time of stirring increases, a conversion ratio from the starting materials to the solid electrolyte increases. Subsequently, the mixture obtained from the melt quenching method or the mechanical milling method is heat-treated at a predetermined temperature, and then the resultant is pulverized to prepare a solid electrolyte in the form of particles. When the solid electrolyte has glass transition characteristics, the solid electrolyte may be changed from amorphous to crystalline by the heat-treatment.

The thus obtained solid electrolyte may be deposited by using a commonly known method, for example, an aerosol deposition method, a cold spray method, or a sputtering method to prepare a solid electrolyte layer 30. In an embodiment, the solid electrolyte layer 30 may be prepared by pressing a plurality of the solid electrolyte particles. In an embodiment, the solid electrolyte layer 30 may be prepared by mixing a solid electrolyte, a solvent, and a binder to prepare a mixture and then coating, drying, and pressing the mixture.

Preparation of All-Solid Secondary Battery

The cathode layer 10, the anode layer 20, and the solid electrolyte layer 30 prepared as described above may be stacked such that the solid electrolyte layer 30 is between the cathode layer 10 and the anode layer 20 to prepare a stack, and the stack may be pressed to prepare an all-solid secondary battery 1. The pressing of the stack may be omitted.

In an embodiment, the anode layer 20 having a structure of the first anode active material layer 22/second anode active material layer 24/anode current collector 21 may be disposed on the solid electrolyte layer 30 such that the first anode active material layer 22 contacts the solid electrolyte layer 30, and the resultant may be pressed to prepare a solid electrolyte layer 30/anode layer 20 stack. The pressing process may be performed by, for example, cold isostatic pressing (CIP). A pressing temperature may be room temperature. The pressing temperature may be, for example, about 40° C. or lower or about 30° C. or lower. The pressing temperature may be, for example, about 10° C. to about 40° C., about 20° C. to about 30° C., or about 25° C. A pressure of the pressing process may be about 400 MPa or lower, about 350 MPa or lower, about 300 MPa or lower, or about 250 MPa or lower. A pressure of the pressing process may be in a range of about 1 MPa to about 400 MPa, about 10 MPa to about 400 MPa, about 100 MPa to about 400 MPa, about 100 MPa to about 350 MPa, about 100 MPa to about 300 MPa, or about 100 MPa to about 250 MPa. Subsequently, a cathode layer 10 may be disposed on the solid electrolyte layer 30 of the solid electrolyte layer 30/anode layer 20 stack, and the resultant may be pressed to prepare an all-solid secondary battery 1. The pressing process may be performed by, for example, cold isostatic pressing (CIP). The pressing conditions may be, for example, within the same ranges with those of the pressing of the solid electrolyte layer 30/anode layer 20 stack.

In an embodiment, the releasable substrate/first anode active material layer 22 stack may be disposed on the solid electrolyte layer 30 such that the first anode active material layer 22 contacts the solid electrolyte layer 30, and the resultant may be pressed to prepare a solid electrolyte layer 30/first anode active material layer 22/releasable substrate (SUS) stack. The pressing process may be performed by, for example, cold isostatic pressing (CIP). The pressing conditions may be, for example, within the same ranges with those of the pressing of the solid electrolyte layer 30/anode layer 20 stack. The releasable substrate may be removed from the solid electrolyte layer 30/first anode active material layer 22/releasable substrate (SUS) stack. Then, the anode current collector 21/second anode active material layer 24 may be disposed on the first anode active material layer 22 of the solid electrolyte layer 30/first anode active material layer 22 stack such that a lithium metal layer, which is the second anode active material layer 24, contacts the first anode active material layer 22, and the resultant may be pressed to prepare a solid electrolyte layer 30/anode layer 20 stack. The pressing process may be performed by, for example, cold isostatic pressing (CIP). A pressing temperature may be room temperature. The pressing temperature may be, for example, about 40° C. or lower or about 30° C. or lower. The pressing temperature may be, for example, about 10° C. to about 40° C., about 20° C. to about 30° C., or about 25° C. A pressure of the pressing process may be about 400 MPa or lower, about 350 MPa or lower, about 300 MPa or lower, or about 250 MPa or lower. A pressure of the pressing process may be in a range of about 1 MPa to about 400 MPa, about 10 MPa to about 390 MPa, about 100 MPa to about 380 MPa, about 150 MPa to about 350 MPa, about 200 MPa to about 325 MPa, or about 225 MPa to about 300 MPa. Subsequently, a cathode layer 10 may be disposed on the solid electrolyte layer 30 of the solid electrolyte layer 30/anode layer 20 stack, and the resultant may be pressed to prepare an all-solid secondary battery 1. The pressing process may be performed by, for example, cold isostatic pressing (CIP). The pressing conditions may be, for example, within the same ranges with those of the pressing of the solid electrolyte layer 30/anode layer 20 stack.

A composition and a preparation method of the all-solid secondary battery 1 are examples of embodiments, where elements of the composition and processes of the preparation method may be appropriately modified.

One or more exemplary embodiments will now be described with reference to the following examples. However, these examples are not intended to limit the scope of the present disclosure.

EXAMPLES

Preparation of All-Solid Secondary Battery

Example 1: 15% of PYR13FSI (2M Li Salt), First Anode Active Material Layer (Ag+CB) Having a Thickness of 7 μm, Second Anode Active Material Layer (Li Metal Layer), and NCM Cathode Preparation of Solid Electrolyte Layer/Anode Stack Carbon black (CB 35) having a primary particle diameter of about 38 nm and silver (Ag) particles having an average particle diameter of about 60 nm were prepared as an anode active material.

An organic electrolyte was prepared by dissolving 2.0 M of LiFSi in an organic salt represented by Formula 13, N-propyl-N-methyl-pyrrolidinium bis(fluorosulfonyl)imide (PYR13FSI), and a composition was prepared using the organic electrolyte.

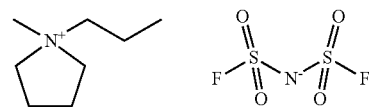

Formula 13

3 g of carbon black (CB 35), 1 g of silver particles, and 0.03 g of organic electrolyte were added to a container, and 4 g of a N-methylpyrrolidone (NMP) solution including 5 wt % of a PVDF binder (#9300 of Kureha Corp.) was added thereto to prepare a solution mixture. Then, the solution mixture was stirred while adding NMP in a small amount to the solution mixture to prepare a slurry. The NMP was added until a viscosity of the slurry was appropriate to film formation by a blade coater.

The prepared slurry was coated on a stainless steel (SUS) foil using a bar coater and dried in the air at a temperature of about 80° C. for about 20 minutes. A stack thus obtained was vacuum dried at a temperature of about 100° C. for about 12 hours. The dried stack was roll-pressed at room temperature to flatten a surface of a first anode active material layer of the stack. A SUS/first anode active material layer stack was prepared using these processes. A thickness of the first anode active material layer was about 7 μm.

An amount of the organic electrolyte (LiFSI+PYR13FSI) with respect to 100 parts by weight of the PVDF binder in the first anode active material layer was about 15 parts by weight.

An amount of the organic electrolyte (LiFSI+PYR13FSI) with respect to 100 parts by weight of the anode active material (carbon black+silver particles) in the first anode active material layer was about 0.75 parts by weight.

A lithium metal layer having a thickness of about 20 μm was coated on a copper (Cu) foil having a thickness of about 10 μm to prepare a lithium metal layer/Cu stack.

The SUS/first anode active material layer stack was disposed such that the first anode active material layer contacts the lithium metal layer on the lithium metal layer of the prepared lithium metal layer/Cu stack, a pressure of about 250 MPa was applied thereto at a temperature of 25° C. using a cold isostatic pressing (CIP) method to prepare a Cu/lithium metal layer/first anode active material layer/SUS stack. The SUS substrate was removed from the prepared stack.

A LLZO ($Li_7La_3Zr_2O_{12}$) pellet having a thickness of about 495 μm was prepared as a solid electrolyte layer.

The Cu/lithium metal layer/first anode active material layer was disposed on a solid electrolyte layer such that the first anode active material layer contacts the solid electrolyte layer, and a pressure of about 250 MPa was applied thereto at a temperature of 25° C. using a CIP method to prepare a Cu/lithium metal layer/first anode active material layer/solid electrolyte layer stack was prepared. A solid electrolyte layer/anode stack was prepared.

Preparation of Cathode $LiNi_{1/3}Co_{1/3}Mn_{1/3}O_2$ (NCM) was prepared as a cathode active material and polytetrafluoroethylene (a Teflon binder available from DuPont) was prepared as a binder. Also, carbon nanofibers (CNFs) were prepared as a conductive agent. Next, the cathode active material, the conductive agent, and the binder were mixed at a weight ratio of about 100:2:1. The mixture was stretched to a shape of sheet to prepare a cathode active material sheet (or layer). The prepared cathode active material sheet was pressed on a cathode current collector formed of an aluminum foil having a thickness of about 18 μm to prepare a cathode. A thickness of the cathode active material layer was about 4 mm. The cathode active material layer of the cathode was impregnated in an organic electrolyte and used in preparation of an all-solid secondary battery. The organic electrolyte was prepared by dissolving 2.0 M of LiFSI in an organic salt, N-propyl-N-methyl-pyrrolidinium bis(fluorosulfonyl) imide) (PYR13FSI).

Preparation of All-Solid Secondary Battery

A cathode was disposed such that the cathode active material layer faced upward in a SUS cap. The solid electrolyte layer/anode stack was disposed such that the solid electrolyte layer was disposed on the cathode active material layer, and the resultant was sealed to prepare an all-solid secondary battery. The cathode and an anode were insulated with an insulator. A part of the cathode current collector and a part of an anode current collector were protruded to the outside of the sealed battery and respectively used as a cathode terminal and an anode terminal.

Example 2: 30% of PYR13FSI (2M Li Salt), First Anode Active Material Layer (Ag+CB) Having a Thickness of 7 μm, Second Anode Active Material Layer (Li Metal Layer), and NCM Cathode An all-solid secondary battery was prepared in the same manner as in Example 1, except that an amount of the organic electrolyte was changed to about 30 parts by weight with respect to 100 parts by weight of a PVDF binder. A thickness of the first anode active material layer was about 7 μm as the same in Example 1.

Example 3: 10% of PYR13FSI (2M Li Salt), First Anode Active Material Layer (Ag+CB) Having a Thickness of 8 μm, Second Anode Active Material Layer (Li Metal Layer), and NCM Cathode An all-solid secondary battery was prepared in the same manner as in Example 1, except that an amount of the organic electrolyte was changed to about 10 parts by weight with respect to 100 parts by weight of a PVDF binder, and a thickness of the first anode active material layer to about 8 μm.

Example 4: 5% of PYR13FSI (2M Li Salt), First Anode Active Material Layer (Ag+CB) Having a Thickness of 8 μm, Second Anode Active Material Layer (Li Metal Layer), and NCM Cathode An all-solid secondary battery was prepared in the same manner as in Example 1, except that an amount of the organic electrolyte was changed to about 5 parts by weight with respect to 100 parts by weight of a PVDF binder, and a thickness of the first anode active material layer to about 8 μm.

Example 5: 40% of PYR13FSI (2M Li Salt), First Anode Active Material Layer (Ag+CB) Having a Thickness of 9 μm, Second Anode Active Material Layer (Li Metal Layer), and NCM Cathode An all-solid secondary battery was prepared in the same manner as in Example 1, except that an amount of the organic electrolyte was changed to about 40 parts by weight with respect to 100 parts by weight of a PVDF binder, and a thickness of the first anode active material layer to about 9 μm.

Example 6: 15% of IMDFSI (2M Li Salt), First Anode Active Material Layer (Ag+CB) Having a Thickness of 10 μm, Second Anode Active Material Layer (Li Metal Layer), and NCM Cathode An all-solid secondary battery was prepared in the same manner as in Example 1, except that an organic salt was changed to N-methyl-N-ethyl-imidazolium bis(fluorosulfonyl)imide (IMDFSI) represented by Formula 14 instead of PYR13FSI, and a thickness of the first anode active material layer to about 10 μm.

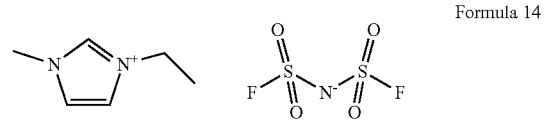

Formula 14

Example 7: 15% of PYR13FSI (2M Li Salt), First Anode Active Material Layer (Ag+CB) Having a Thickness of 7 μm, Second Anode Active Material Layer (Li Metal Layer), and LCO Cathode An all-solid secondary battery was prepared in the same manner as in Example 1, except that a cathode active material was changed to $LiCoO_2$ (LCO) from $LiNi_{0.8}Co_{0.15}Mn_{0.05}O_2$ (NCM). A thickness of the first anode active material layer was about 7 μm as the same in Example 1.

Example 8: 15% of PYR13FSI (2M Li Salt), First Anode Active Material Layer (Ag+CB) Having a Thickness of 7 μm, No Second Anode Active Material Layer (Deposition Type), and NCM Cathode Preparation of Solid Electrolyte Layer/Anode Stack A SUS/first anode active material layer was prepared in the same manner as in Example 1.

A $Li_7La_3Zr_2O_{12}$ (LLZO) pellet having a thickness of about 495 μm was prepared as a solid electrolyte layer.

The SUS/first anode active material layer was disposed such that the first anode active material layer contacts the solid electrolyte layer on a surface of the solid electrolyte layer, and a pressure of about 250 MPa was applied thereto at a temperature of 25° C. using a CIP method to prepare a solid electrolyte layer/first anode active material layer/SUS stack. The SUS substrate was removed from the stack.

A copper (Cu) foil having a thickness of about 10 μm was prepared.

The Cu foil was disposed on the first anode active material layer of the solid electrolyte layer/first anode active material layer stack, and a pressure of about 250 MPa was applied thereto at a temperature of 25° C. using a CIP method to prepare a Cu/first anode active material layer/solid electrolyte layer stack. A solid electrolyte layer/anode stack was prepared.

Preparation of Cathode

A cathode was prepared in the same manner as in Example 1.

Preparation of All-Solid Secondary Battery

A cathode was disposed such that the cathode active material layer faces upward in a SUS cap. The solid electrolyte layer/anode stack was disposed such that the solid electrolyte layer was disposed on the cathode active material layer, and the resultant was sealed to prepare an all-solid secondary battery. The cathode and an anode were insulated with an insulator. A part of the cathode current collector and a part of an anode current collector protruded to the outside of the sealed battery and respectively used as a cathode terminal and an anode terminal.

Example 9: 15% of PYR13FSI (2M Li Salt), First Anode Active Material Layer (CB Alone) Having a Thickness of 7 μm, Second Anode Active Material Layer (Li Metal Layer), and NCM Cathode An all-solid secondary battery was prepared in the same manner as in Example 1, except that an anode active material was changed to 4 g of carbon black (CB 35) (not using Ag) instead of a mixture of 3 g of carbon black (CB 35) and 1 g of silver particles. A thickness of the first anode active material layer was about 7 μm as the same in Example 1.

Comparative Example 1: 0% of PYR13FSI (2M Li Salt), First Anode Active Material Layer Having a Thickness of 8 μm, Second Anode Active Material Layer (Li Metal Layer), and NCM Cathode Preparation of Solid Electrolyte Layer/Anode Stack A SUS/first anode active material layer stack was prepared in the same manner as in Example 1, except that an organic electrolyte was not added.

A $Li_7La_3Zr_2O_{12}$ (LLZO) pellet having a thickness of about 495 μm was prepared as a solid electrolyte layer.

The SUS/first anode active material layer was disposed such that the first anode active material layer contacts the solid electrolyte layer on a surface of the solid electrolyte layer, and a pressure of about 250 MPa was applied thereto at a temperature of 25° C. using a CIP method to prepare a solid electrolyte layer/first anode active material layer/SUS stack. The SUS substrate was removed from the stack.

A lithium metal layer having a thickness of about 20 μm was coated on a copper (Cu) foil having a thickness of about 10 μm to prepare a lithium metal layer/Cu stack.

A lithium metal layer/Cu stack was disposed on the first anode active material layer of the solid electrolyte layer/first anode active material layer stack such that the lithium metal layer contacts the first anode active material layer, and a pressure of about 250 MPa was applied thereto at a temperature of 25° C. using a CIP method to prepare a Cu/lithium metal layer/first anode active material layer/solid electrolyte layer stack. A solid electrolyte layer/anode stack was prepared.

Preparation of Cathode

A cathode was prepared in the same manner as in Example 1.

Preparation of All-Solid Secondary Battery

A cathode was disposed such that the cathode active material layer faces upward in a SUS cap. The solid electrolyte layer/anode stack was disposed such that the solid electrolyte layer was disposed on the cathode active material layer, and the resultant was sealed to prepare an all-solid secondary battery. The cathode and an anode were insulated with an insulator. A part of the cathode current collector and a part of an anode current collector were protruded to the outside of the sealed battery and respectively used as a cathode terminal and an anode terminal.

Comparative Example 2: 60% of PYR13FSI (2M Li Salt), First Anode Active Material Layer Having a Thickness of 8 μm, Second Anode Active Material Layer (Li Metal Layer), and NCM Cathode An all-solid secondary battery was prepared in the same manner as in Example 1, except that an amount of the organic electrolyte was changed to about 60 parts by weight based on 100 parts by weight of the PVDF binder, and a thickness of the first anode active material layer to about 8 μm.

When the amount of the organic electrolyte is too high, a SUS/first anode active material layer stack having a regular shape was not formed. Thus, an all-solid secondary battery was not prepared.

Evaluation Example 1: Interfacial Resistance Evaluation

Interfacial resistance of the all-solid secondary batteries prepared in Examples 1 to 9 and Comparative Example 1 were measured, and the results are shown in Table 1.

The interfacial resistance (ohm square centimeter, $\Omega\cdot cm^2$) were obtained from the real impedance measurements of the all-solid secondary batteries as measured by a Solartron 1400A/1455A impedance analyzer using a 2-probe method. The frequency range was in a range of about 0.1 Hz to about 1 MHz, and the amplitude voltage was about 10 mV. The measurement was performed in the air atmosphere at about 25° C. The Nyquist plot of the impedance measurement results with respect to the all-solid secondary batteries of Example 1 and Comparative Example 1 is shown in FIG. 1.

TABLE 1

| | Interfacial resistance [$\Omega \cdot cm^2$] |
|---|---|
| Example 1 | 28 |
| Example 2 | 31 |
| Example 3 | 59 |
| Example 4 | 57 |
| Example 5 | 61 |
| Example 6 | 68 |
| Example 7 | 38 |
| Example 8 | 25 |
| Comparative Example 1 | 78 |

As shown in Table 1 and FIG. 1, the interfacial resistance of the all-solid secondary batteries of Examples 1 to 8 including an organic electrolyte decreased compared to that of the all-solid secondary battery of Comparative Example 1, which does not include an organic electrolyte.

Therefore, when the first anode active material layer including an organic electrolyte is used in the all-solid secondary batteries of Examples 1 to 8, it was confirmed that an interfacial resistance between the solid electrolyte layer and anode decreased.

Evaluation Example 2: Limiting Current Density Evaluation

Current density characteristics of the all-solid secondary batteries prepared in Examples 1 to 9 and Comparative Example 1 were evaluated by the following charge/discharge test, and some of the results are shown in Table 2. The charge/discharge test was performed with the all-solid secondary batteries each placed in a constant-temperature chamber of 25° C.

Charge/discharge cycles were performed while increasing a current density from the $1^{st}$ cycle to the $5^{th}$ cycle. A current density at a cycle right before the cycle in which a short-circuit occurred was considered as a limiting current density.

When a short-circuit did not occur until the $5^{th}$ cycle, a current density at the $5^{th}$ cycle was considered as a limiting current density.

The $1^{st}$ cycle included charging the battery with a constant current of about 0.3 mA/cm² for about 12.5 hours until a battery voltage was about 4.2 V (vs. Li). Next, the battery was discharged with a constant current of about 0.5 mA/cm² for about 12.5 hours until a battery voltage was about 2.85 V (vs. Li).

The $2^{nd}$ cycle included charging the battery with a constant current of about 0.6 mA/cm² for about 12.5 hours until a battery voltage was about 4.2 V (vs. Li). Next, the battery was discharged with a constant current of about 0.5 mA/cm² for about 12.5 hours until a battery voltage was about 2.85 V (vs. Li).

The $3^{rd}$ cycle included charging the battery with a constant current of about 1.0 mA/cm² for about 12.5 hours until a battery voltage was about 4.2 V (vs. Li). Next, the battery was discharged with a constant current of about 0.5 mA/cm² for about 12.5 hours until a battery voltage was about 2.85 V (vs. Li).

The $4^{th}$ cycle included charging the battery with a constant current of about 1.6 mA/cm² for about 12.5 hours until a battery voltage was about 4.2 V (vs. Li). Next, the battery was discharged with a constant current of about 0.5 mA/cm² for about 12.5 hours until a battery voltage was about 2.85 V (vs. Li).

The $5^{th}$ cycle included charging the battery with a constant current of about 2.0 mA/cm² for about 12.5 hours until a battery voltage was about 4.2 V (vs. Li). Next, the battery was discharged with a constant current of about 0.5 mA/cm² for about 12.5 hours until a battery voltage was about 2.85 V (vs. Li).

TABLE 2

|  | Limiting current density [mA/cm²] |
|---|---|
| Example 1 | 2.0 |
| Example 2 | 1.6 |
| Example 3 | 1.6 |
| Example 4 | 1.6 |
| Example 5 | 0.8 |
| Example 6 | 0.6 |
| Example 7 | 1.6 |
| Comparative Example 1 | 0.3 |

As shown in Table 2, the limiting current densities of the all-solid secondary batteries of Examples 1 to 7 including an organic electrolyte increased compared to that of the all-solid secondary battery of Comparative Example 1 not including an organic electrolyte.

Therefore, short-circuit occurrence at a high current density was suppressed in the all-solid secondary batteries of Examples 1 to 7 by including the first anode active material layer including an organic electrolyte.

The increase in the limiting current density was deemed as due to improved uniformity of lithium deposited in the anode or dissolved from the anode in a charge/discharge process.

Evaluation Example 3: Cycle Characteristic Evaluation

Figure 2:
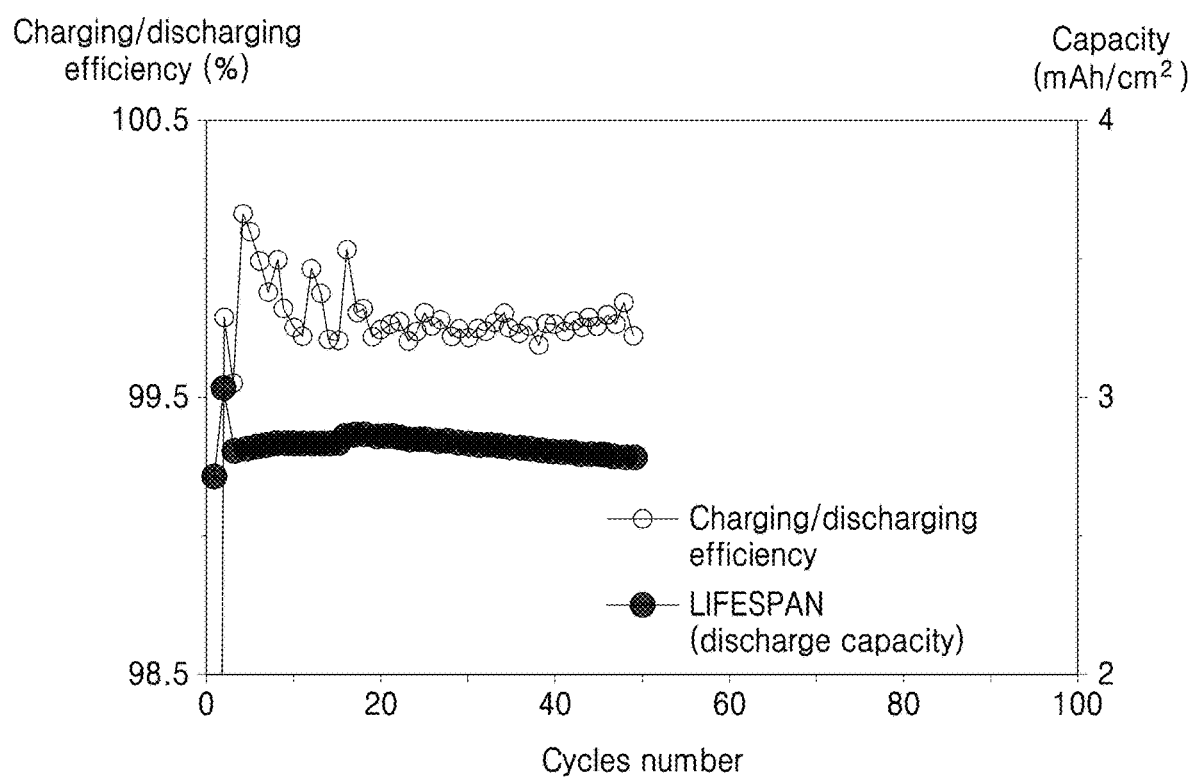
FIG. 2 is a graph of a charge/discharge efficiency (%) and discharge capacity (mAh/cm$^2$) of the all-solid secondary battery of Example 1.

Cycle characteristics of the all-solid secondary batteries prepared in Examples 1 to 9 were evaluated by the following charge/discharge test, and some of the results are shown in FIG. 2. The charge/discharge test was performed with the all-solid secondary batteries each placed in a constant-temperature chamber of 25° C.

The $1^{st}$ cycle included charging the battery with a constant current of about 0.6 mA/cm² until a battery voltage was about 4.2 V (vs. Li), and subsequently the current was cut-off at 0.3 mA/cm² while maintaining 4.2 V (vs. Li) in a constant voltage mode. Next, the battery was discharged with a constant current of about 0.6 mA/cm² until a battery voltage was about 2.85 V (vs. Li).

The $2^{nd}$ to $50^{th}$ cycle included charging with a constant current of about 1.0 mA/cm² until a battery voltage was about 4.2 V (vs. Li), and subsequently the current was cut-off at 0.3 mA/cm² while maintaining 4.2 V (vs. Li) in a constant voltage mode. Next, the battery was discharged with a constant current of about 1.0 mA/cm² until a battery voltage was about 2.85 V (vs. Li).

A charge/discharge efficiency and a discharge capacity of the all-solid secondary battery of Example 1 are shown in FIG. 2.

As shown in FIG. 2, the all-solid secondary battery of Example had almost no decrease of the charge/discharge efficiency and discharge capacity up to the $50^{th}$ cycle. A capacity retention rate at the $50^{th}$ cycle defined the same as in Equation 1 was about 99.87%.

Capacity retention (%)=[Discharge capacity of $50^{th}$ cycle/discharge capacity of $1^{st}$ cycle]×100%   Equation 1

It was confirmed that the all-solid secondary battery of Example 1 provided excellent charge/discharge efficiency and lifespan characteristics.

Evaluation Example 4: Electrode State Evaluation

Figure 3A:
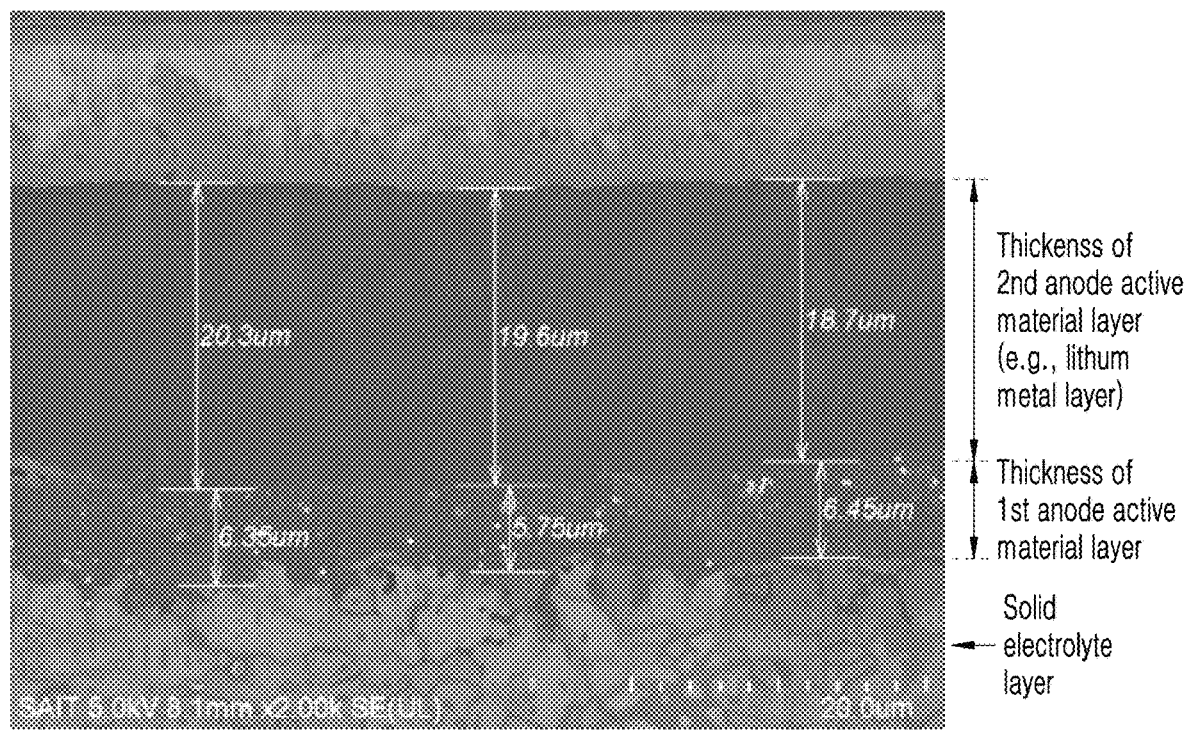
FIG. 3A is a scanning electron microscope (SEM) image of a cross-section of the all-solid secondary battery of Example 1 after 7 charge/discharge cycles.
Figure 3B:
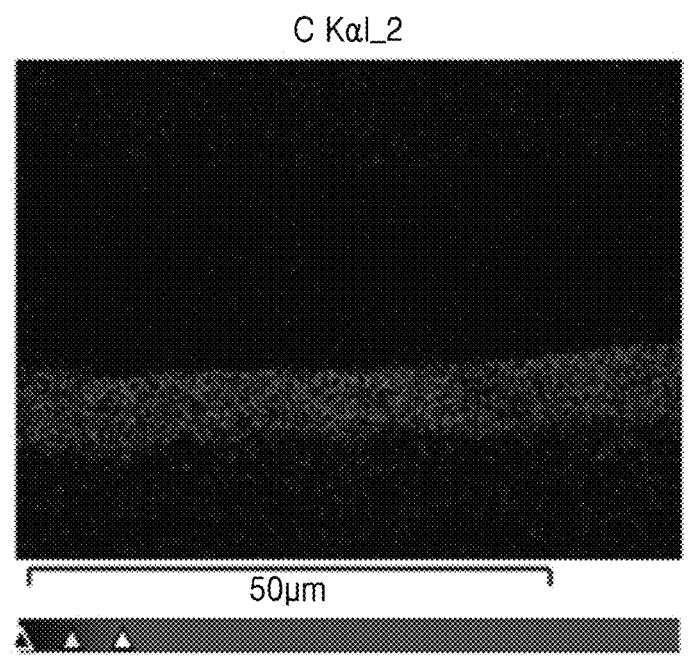
FIG. 3B is an energy dispersive X-ray spectroscopy (EDS) carbon elemental mapping image of the cross-section of the all-solid secondary battery of Example 1 after 7 charge/discharge cycles.
Figure 3C:
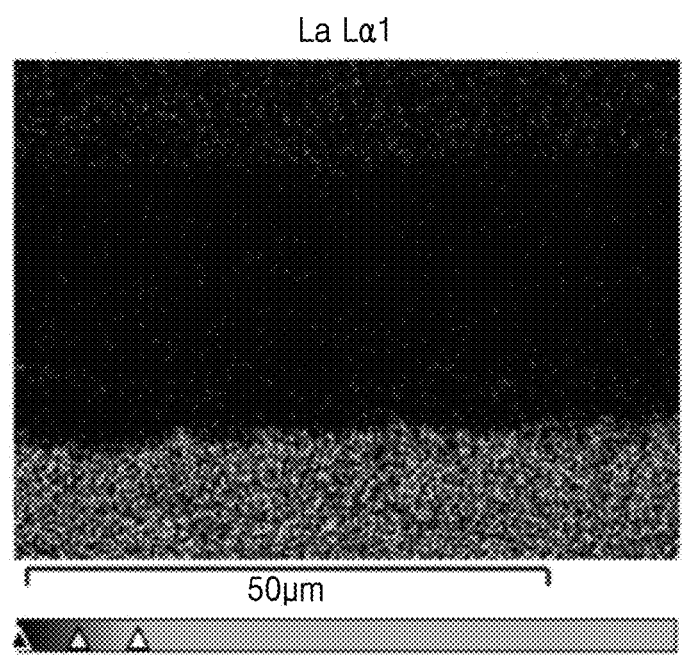
FIG. 3C is an EDS lanthanum elemental mapping image of the cross-section of the all-solid secondary battery of Example 1 after 7 charge/discharge cycles.
Figure 3D:
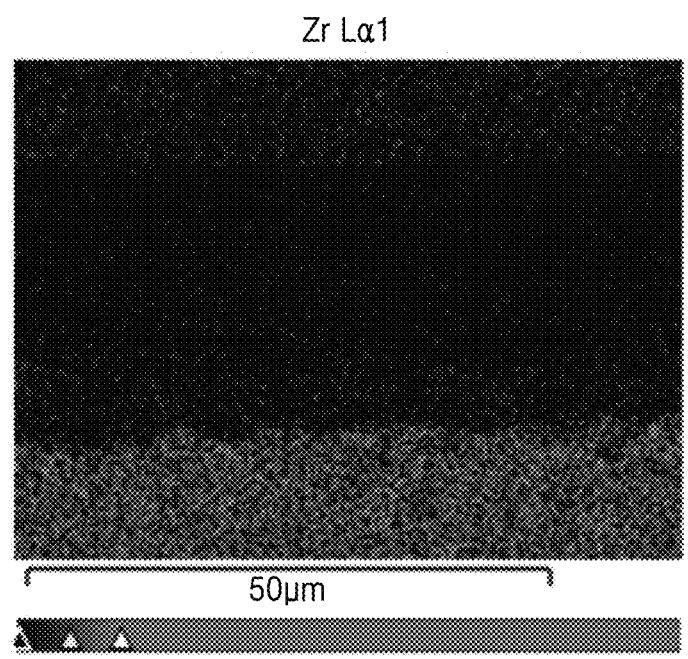
FIG. 3D is an EDS zirconium elemental mapping image of the cross-section of the all-solid secondary battery of Example 1 after 7 charge/discharge cycles.

High-angle annular dark field image (HAADF) scanning electron microscope (SEM) images and the energy dispersive X-ray spectroscopy (EDS) element mapping images of a cross-section of the all-solid secondary battery of Example 1 used in the charge/discharge process of Evaluation Example 3 after discharging in the $7^{th}$ cycle are shown in FIGS. 3A and 3D.

As shown in FIG. 3A, it was confirmed that a structure in which the first anode active material layer and the lithium metal layer were stacked on the lower-most solid electrolyte layer after the $7^{th}$ charge/discharge cycle was stable.

As shown in FIG. 3B, it was confirmed that carbon is uniformly distributed throughout the entire first anode active material layer.

As shown in FIGS. 3C and 3D, La and Zr are uniformly distributed throughout the solid electrolyte layer.

As described above, the all-solid secondary battery according to an embodiment may be used in various portable devices and vehicles.

According to an embodiment, when the first anode active material layer includes an organic electrolyte, short-circuits may be prevented, and a lithium battery having improved lifespan characteristics may be provided as a result.

It should be understood that embodiments described herein should be considered in a descriptive sense only and not for purposes of limitation. Descriptions of features, aspects, or advantages within each embodiment should be considered as available for other similar features, aspects, or advantages in other embodiments. While one or more embodiments have been described with reference to the figures, it will be understood by those of ordinary skill in the art that various changes in form and details may be made therein without departing from the spirit and scope as defined by the following claims.

What is claimed is:

1. An all-solid secondary battery comprising:
a cathode layer comprising a cathode active material layer;
an anode layer; and
a solid electrolyte layer disposed between the cathode layer and the anode layer,
wherein the anode layer comprises an anode current collector and a first anode active material layer disposed on the anode current collector,
wherein the first anode active material layer comprises an organic electrolyte and an anode active material that is capable of forming an alloy with lithium or a compound with lithium,
wherein the anode active material comprises at least one of a carbon-containing anode active material, a metal anode active material, or metalloid anode active material,
wherein the first anode active material layer comprises the organic electrolyte in a range from about 0.1 parts by weight to about 2.5 parts by weight, based on 100 parts by weight of the anode active material,
wherein the organic electrolyte comprises an organic salt comprising an organic cation and an anion, and
wherein the organic cation comprises a heterocyclic cation comprising 1 to 3 heteroatoms.

2. The all-solid secondary battery of claim 1, wherein the organic salt comprises a compound represented by Formula 2:

Formula 2 wherein, in Formula 2,

is a heterocycloalkyl or heteroaryl ring comprising 1 to 3 heteroatoms and 2 to 30 carbon atoms, wherein the ring is unsubstituted or substituted with a substituent group,
$X_2$ is —N($R_5$)($R_6$)—, —N($R_5$)═, —P($R_5$)═, or —P($R_5$)($R_6$)—,
the substituent group substituted in the ring, $R_5$, and $R_6$ are each independently hydrogen, an unsubstituted or halogen-substituted C1-C30 alkyl group, an unsubstituted or halogen-substituted C1-C30 alkoxy group, an unsubstituted or halogen-substituted C6-C30 aryl group, an unsubstituted or halogen-substituted C6-C30 aryloxy group, an unsubstituted or halogen-substituted C3-C30 heteroaryl group, an unsubstituted or halogen-substituted C3-C30 heteroaryloxy group, an unsubstituted or halogen-substituted C4-C30 cycloalkyl group, or an unsubstituted or halogen-substituted C3-C30 heterocycloalkyl group, and
$Y^-$ is an anion.

3. The all-solid secondary battery of claim 1, wherein the organic salt comprises a compound represented by at least one of Formula 4:

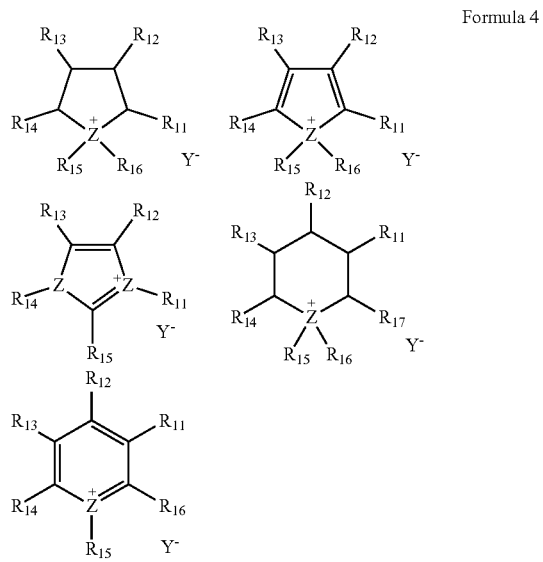

Formula 4 wherein, in Formula 4,

Z is N or P, $R_{11}$, $R_{12}$, $R_{13}$, $R_{14}$, $R_{15}$, $R_{16}$, and $R_{17}$ are each independently hydrogen, an unsubstituted or halogen-substituted C1-C30 alkyl group, an unsubstituted or halogen-substituted C6-C30 aryl group, an unsubstituted or halogen-substituted C3-C30 heteroaryl group, an unsubstituted or halogen-substituted C4-C30 cycloalkyl group, or an unsubstituted or halogen-substituted C3-C30 heterocycloalkyl group, and $Y^-$ is an anion.

4. The all-solid secondary battery of claim 1, wherein the organic salt comprises a compound represented by at least one of Formulae 6 to 10:

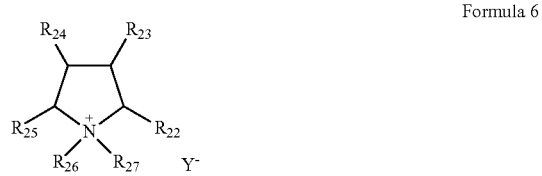

Formula 6

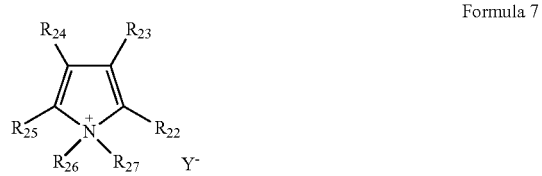

Formula 7

Formula 8

Formula 9

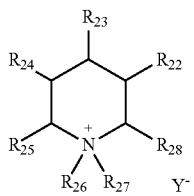

Formula 10

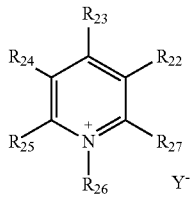

wherein, in Formulae 6 to 10,
$R_{22}$, $R_{23}$, $R_{24}$, $R_{25}$, $R_{26}$, $R_{27}$, and $R_{28}$ are each independently hydrogen, an unsubstituted or halogen-substituted C1-C30 alkyl group, an unsubstituted or halogen-substituted C6-C30 aryl group, an unsubstituted or halogen-substituted C3-C30 heteroaryl group, an unsubstituted or halogen-substituted C4-C30 cycloalkyl group, or an unsubstituted or halogen-substituted C3-C30 heterocycloalkyl group, and Y⁻ is an anion.

5. The all-solid secondary battery of claim 1, wherein the organic salt comprises:
at least one of a pyrrolidinium cation, a pyridinium cation, a pyrimidinium cation, an imidazolium cation, a piperidinium cation, a pyrazolium cation, an oxazolium cation, a pyridazinium cation, or a triazolium cation; and
at least one anion.

6. The all-solid secondary battery of claim 1, wherein the organic salt comprises a polymer represented by Formula 11:

Formula 11

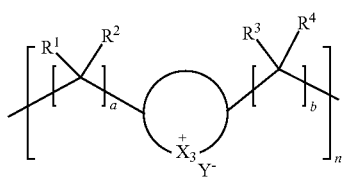

wherein, in Formula 11,

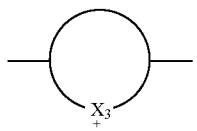

is a heterocycloalkyl or heteroaryl ring comprising 1 to 3 heteroatoms and 2 to 30 carbon atoms, wherein the ring is unsubstituted or substituted with a substituent group,
X is —N($R_5$)($R_6$)—, —N($R_5$)═, —P($R_5$)═, or —P($R_5$)($R_6$)—;
$R^1$ to $R^6$ are each independently an unsubstituted or halogen-substituted C1-C30 alkyl group, an unsubstituted or halogen-substituted C6-C30 aryl group, an unsubstituted or halogen-substituted C3-C30 heteroaryl group, an unsubstituted or halogen-substituted C4-C30 cycloalkyl group, or an unsubstituted or halogen-substituted C3-C30 heterocycloalkyl group,
Y⁻ is an anion,
a and b are each independently an integer from 1 to 5, and
n is an integer from 2 to 2800.

7. The all-solid secondary battery of claim 1, wherein the anion comprises at least one of $BF_4^-$, $PF_6^-$, $AsF_6^-$, $SbF_6^-$, $AlCl_4^-$, $HSO_4^-$, $ClO_4^-$, $CH_3SO_3$, $CF_3CO_2^-$, $Cl^-$, $Br^-$, $I^-$, $BF_4^-$, $SO_4^-$, bis(oxalate) borate, $CF_3SO_3$, $CF_3CO_2$, $(C_2F_5SO_2)_2N$, $(C_2F_5SO_2)$ $(CF_3SO_2)N^-$, or $(CF_3SO_2)_2N^-$.

8. The all-solid secondary battery of claim 1, wherein the organic electrolyte further comprises a lithium salt,
wherein the lithium salt comprises at least one of $LiPF_6^-$, $LiBF_4^-$, $LiCF_3SO_3$, $Li(CF_3SO_2)_2N$, $LiC_2F_5SO_3$, $Li(FSO_2)_2N$, $LiC_4F_9SO_3$, $LiN(SO_2CF_2CF_3)_2$, or compounds represented by Formulae 11 to 14, Formula 11

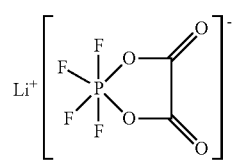

Formula 12

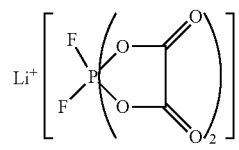

Formula 13

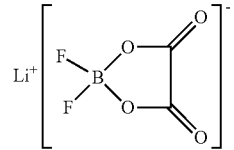

Formula 14

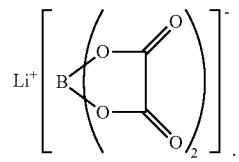

9. The all-solid secondary battery of claim 7, wherein a concentration of a lithium salt in the organic electrolyte is in a range from about 0.01 moles per liter to about 5 moles per liter.

10. The all-solid secondary battery of claim 1, wherein the metal anode active material or metalloid anode active material has a lithium ion diffusion coefficient higher than that of lithium metal.

11. The all-solid secondary battery of claim 1, wherein the metal or metalloid anode active material comprises at least one of indium, silicon, gallium, tin, aluminum, titanium, zirconium, niobium, germanium, antimony, bismuth, gold, platinum, palladium, magnesium, silver, or zinc.

12. The all-solid secondary battery of claim 1, wherein the carbon-containing anode active material comprises amorphous carbon.

13. The all-solid secondary battery of claim 1, wherein the anode active material comprises a mixture of a first particle comprising amorphous carbon and a second particle comprising a metal or a metalloid,
  wherein an amount of the second particles is in a range from about 1 weight percent to about 60 weight percent based on the total weight of the mixture.

14. The all-solid secondary battery of claim 1, wherein the first anode active material layer further comprises a binder, wherein an amount of the organic electrolyte is in a range of about 1 part by weight to about 50 parts by weight based on 100 parts by weight of the binder.

15. The all-solid secondary battery of claim 1, wherein a thickness of the first anode active material layer is in a range from about 1 micrometer to about 50 micrometer,
  wherein an interfacial resistance of the all-solid secondary battery comprising the first anode active material layer obtained by impedance measurement at a temperature of 25° C. is about 70 ohm square centimeter or less.

16. The all-solid secondary battery of claim 1, further comprising a second anode active material layer disposed between the anode current collector and the first anode active material layer or between the solid electrolyte layer and the first anode active material layer,
  wherein the second anode active material layer is a metal layer comprising lithium or a lithium alloy.

17. The all-solid secondary battery of claim 1, wherein the solid electrolyte layer comprises at least one of a sulfide-containing solid electrolyte or an oxide-containing solid electrolyte,
  wherein the oxide-containing solid electrolyte comprises at least one of $Li_{1+x+y}Al_xTi_{2-x}Si_yP_{3-y}O_{12}$, wherein $0<x<2$ and $0\leq y<3$, $BaTiO_3$, $Pb(Zr_aTi_{1-a})O_3$, wherein $0\leq a\leq 1$, $Pb_{1-x}La_xZr_{1-y}Ti_yO_3$, wherein $0\leq x<1$ and $0\leq y<1$, $PB(Mg_{1/3}Nb_{2/3})O_3$—$PbTiO_3$, $HfO_2$, $SrTiO_3$, $SnO_2$, $CeO_2$, $Na_2O$, $MgO$, $NiO$, $CaO$, $BaO$, $ZnO$, $ZrO_2$, $Y_2O_3$, $Al_2O_3$, $TiO_2$, $SiO_2$, $Li_3PO_4^-$, $Li_xTi_y(PO_4)_3$, wherein $0<x<2$ and $0<y<3$, $Li_xAl_yTi_z(PO_4)_3$, wherein $0<x<2$, $0<y<1$, and $0<z<3$, $Li_{1+x+y}(Al_aGa_{1-a})_x(Ti_bGe_{1-b})_{2-x}Si_yP_{3-y}O_{12}$, wherein $0\leq x\leq 1$, $0\leq y\leq 1$, $0\leq a\leq 1$, and $0\leq b\leq 1$, $Li_xLa_yTiO_3$, wherein $0<x<2$ and $0<y<3$, $Li_2O$, $LiOH$, $Li_2CO_3$, $LiAlO_2$, $Li_2O$—$Al_2O_3$—$SiO_2$—$P_2O_5$—$TiO_2$—$GeO_2$, or $Li_{3+x}La_3M_2O_{12}$, wherein M is Te, Nb, or Zr, and $0\leq x\leq 10$.

18. A method of preparing an all-solid secondary battery, the method comprising:
  providing a cathode layer comprising a cathode active material layer;
  providing a first anode active material layer comprising an organic electrolyte and an anode active material that is capable of forming an alloy with lithium or a compound with lithium;
  wherein the anode active material comprises at least one of a carbon-containing anode active material, a metal anode active material, or metalloid anode active material;
  wherein the first anode active material layer comprises the organic electrolyte in a range from about 0.1 parts by weight to about 2.5 parts by weight, based on 100 parts by weight of the anode active material;
  disposing the first anode active material layer on a solid electrolyte layer to prepare a stack; and
  disposing the cathode layer on the solid electrolyte layer of the stack,
  wherein the organic electrolyte comprises an organic salt comprising an organic cation and an anion,
  wherein the organic cation comprises a heterocyclic cation comprising 1 to 3 heteroatoms, and
  wherein an anode layer comprises a current collector and the first anode active material layer.

19. The method of claim 18, further comprising:
  disposing the first anode active material layer on a solid electrolyte layer to prepare a first stack;
  disposing a second anode active material layer on the first anode active material layer to prepare a second stack; and
  disposing a cathode layer on the solid electrolyte layer of the second stack,
  wherein the second anode active material layer comprises a metal layer comprising lithium or a lithium alloy, and
  wherein an anode layer comprises a current collector, the first anode active material layer, and the second anode active material layer.

20. A method of preparing an all-solid secondary battery, the method comprising:
  providing a cathode layer comprising a cathode active material layer;
  providing a first anode active material layer comprising an organic electrolyte and an anode active material that is capable of forming an alloy with lithium or a compound with lithium and a second anode active material layer comprising a metal layer comprising lithium or a lithium alloy;
  wherein the anode active material comprises at least one of a carbon-containing anode active material, a metal anode active material, or metalloid anode active material;
  wherein the first anode active material layer comprises the organic electrolyte in a range from about 0.1 parts by weight to about 2.5 parts by weight, based on 100 parts by weight of the anode active material;
  disposing the first anode active material layer on the second anode active material layer to prepare a first stack;
  disposing a solid electrolyte layer on the first anode active material layer of the first stack to prepare a second stack; and
  disposing the cathode layer on the solid electrolyte layer of the second stack,
  wherein the organic electrolyte comprises an organic salt comprising an organic cation and an anion,
  wherein the organic cation comprises a heterocyclic cation comprising 1 to 3 heteroatoms, and
  wherein an anode layer comprises a current collector, the first anode active material layer, and the second anode active material layer.

* * * * *